US012357617B2

(12) United States Patent
Bulterys et al.

(10) Patent No.: US 12,357,617 B2
(45) Date of Patent: Jul. 15, 2025

(54) DISCOVERY OF NOVEL ANTI-INFECTIVES FOR GRAM NEGATIVE PATHOGENS

(71) Applicant: The Regents of the University of California, Oakland, CA (US)

(72) Inventors: Philip Bulterys, Los Angeles, CA (US); Jeffery F. Miller, Santa Monica, CA (US); Robert D. Damoiseaux, Beverly Hills, CA (US); Christopher Todd French, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1089 days.

(21) Appl. No.: 17/279,015

(22) PCT Filed: Oct. 4, 2019

(86) PCT No.: PCT/US2019/054824
§ 371 (c)(1),
(2) Date: Mar. 23, 2021

(87) PCT Pub. No.: WO2020/072976
PCT Pub. Date: Apr. 9, 2020

(65) Prior Publication Data
US 2022/0031672 A1 Feb. 3, 2022

Related U.S. Application Data

(60) Provisional application No. 62/741,393, filed on Oct. 4, 2018.

(51) Int. Cl.
*A61K 31/436* (2006.01)
*A61P 31/04* (2006.01)
(52) U.S. Cl.
CPC ............ *A61K 31/436* (2013.01); *A61P 31/04* (2018.01)

(58) Field of Classification Search
CPC .............................. A61K 31/436; A61P 31/04
See application file for complete search history.

(56) References Cited

U.S. PATENT DOCUMENTS

2009/0170876 A1    7/2009   Qasem et al.

FOREIGN PATENT DOCUMENTS

WO    2010081049    7/2010

OTHER PUBLICATIONS

PCT International Search Report & Written Opinion dated Feb. 6, 2020 for PCT Application No. PCT/US19/54824.
Maloy, J.P., "Characterization of an Intracellular Flagellar System in Pathogenic Burkholderia Species", University of California, Los Angeles, Jun. 2017, pp. 1-12.

*Primary Examiner* — Kamal A Saeed
(74) *Attorney, Agent, or Firm* — GATES & COOPER LLP

(57) ABSTRACT

*Burkholderia pseudomallei* (Bp) and *Burkholderia mallei* (Bm) are Tier-1 select pathogens that cause highly lethal human infections with limited therapeutic options. Intercellular spread is a hallmark of *Burkholderia* pathogenesis and its prominent ties to virulence make it an attractive therapeutic target. We developed a high-throughput cell-based phenotypic assay and screened ~220,000 small molecules for their ability to disrupt intercellular spread by *Burkholderia thailandensis*, a BSL-2 surrogate for these pathogens. 268 hits were identified, and cross-species validation found 32 hits that also disrupt intercellular spread by Bp and/or Bm. In a fulminant murine model of respiratory melioidosis, treatment with a number of these agents was significantly more effective than ceftazidime, the current drug of choice, for improving patient survival and decreasing bacterial counts in major organs.

6 Claims, 10 Drawing Sheets

DISCOVERY OF NOVEL ANTI-INFECTIVES FOR GRAM NEGATIVE PATHOGENS

CROSS REFERENCE TO RELATED APPLICATIONS

This application claims the benefit under 35 U.S.C. Section 119(e) of commonly-assigned U.S. Provisional Patent Application Ser. No. 62/741,393, filed on Oct. 4, 2018, and entitled "DISCOVERY OF NOVEL ANTI-INFECTIVES FOR GRAM NEGATIVE PATHOGENS" which application is incorporated by reference herein.

STATEMENT REGARDING FEDERALLY SPONSORED RESEARCH AND DEVELOPMENT

This invention was made with government support under Grant Number AI065359, awarded by the National Institutes of Health and Grant Number HDTRA1-11-1-0003, awarded by the U.S. Department of Defense, Defense Threat Reduction Agency. The government has certain rights in the invention.

TECHNICAL FIELD

The present invention provides methods and materials pertaining to anti-infectives for gram negative pathogens.

BACKGROUND OF THE INVENTION

*Burkholderia pseudomallei* (Bp) and *Burkholderia mallei* (Bm), the etiologic agents of melioidosis and glanders, respectively, are highly infectious Gram-negative bacteria for which limited therapeutic options exist. Bp normally inhabits the rhizosphere (1, 2) and can be acquired by humans and other mammals via inhalation, ingestion, or percutaneous inoculation (3, 4). Individuals regularly exposed to soil and water in endemic areas are disproportionately affected. The severity of disease varies from chronic infection mimicking tuberculosis to acute, rapidly disseminating sepsis. Clinical management is complicated by intrinsic and acquired mechanisms of antibiotic resistance (5-7), and mortality rates are high despite appropriate diagnosis and treatment (3). Bm is an evolutionary descendent of Bp (8) with a restricted host range that primarily includes solidungulates, although it can also cause life-threatening zoonotic infections in humans (9, 10). In light of their low infectious doses, high lethality, extensive antibiotic resistance, and the lack of protective vaccines, Bm and Bp are classified as Tier 1 select agent pathogens. Concern over malign release against civilian or military targets is heightened in light of their historical use as bioweapons (11, 12). A third, less-pathogenic member of the *Pseudomallei*-group *Burkholderia*, *B. thailandensis* (Bt) shares highly conserved virulence mechanisms with its pathogenic relatives, making it a useful BSL-2 surrogate (13-15).

Although the true global burden of melioidosis is unknown, recent estimates suggest that Bp is endemic in at least 79 countries and is responsible for 165,000 annual human infections, of which 54% are fatal (16). Highly endemic areas include northeast Thailand, where Bp is the leading cause of community-acquired bacteremia, and the Northern Territory of Australia, where Bp is the most common cause of fatal community-acquired bacteremic pneumonia (11, 17-19). The current treatment regimen for melioidosis consists of an initial parenteral phase lasting 10-14 days, aimed at preventing death, followed by an oral eradication phase lasting >3 months, aimed at preventing relapse. Ceftazidime and carbapenems are the mainstays for acute phase therapy, while trimethoprim-sulfamethoxazole (cotrimoxazole) or amoxicillin-clavulanic acid (coamoxiclav) are the choices for eradication phase therapy (11, 17, 18). The efficacy of current treatment regimens is limited, however, by Bp's multitude of intrinsic and acquired drug resistance mechanisms (20-22). The consequences of naturally occurring disease, the potential for nefarious use, and extensive drug resistance make the development of new countermeasures a high priority.

*Pseudomallei*-group *Burkholderia* species can parasitize mammalian cells, and their ability to replicate intracellularly and spread from cell-to-cell is an essential virulence trait (23). Following entry by phagocytosis or invasion, bacteria escape from endocytic vesicles using the activity of the Bsa type III secretion system (T3SSBsa) (FIG. 1). Bacteria then multiply in the cytoplasm, polymerize actin, move through the cytoplasm and spread to neighboring cells by a process involving membrane fusion (24, 25), creating a portal for direct passage of bacteria into neighboring cytosolic compartments (26). Membrane fusion requires the activity of a type VI secretion system (T6SS-5), and multiple cell fusion events result in the formation of large, multinucleated cells (MNCs) which eventually lyse to form plaques on cell monolayers (26). Work by our group and others has shown that *Burkholderia* are able to fuse both phagocytic and non-phagocytic cells (27), and this ability correlates with virulence by Bp and Bm (23, 26, 28, 29). Fusion-mediated cell-cell spread is a unique virulence mechanism for a bacterial pathogen and a novel target for intervention (25, 30).

Unfortunately, target-based screening campaigns against Gram-negative bacteria have been largely unsuccessful due to the inability of many small molecules to penetrate the outer membrane (31-33). Furthermore, prior efforts to develop therapeutics against *Burkholderia* have shown that despite having activity in vitro, compounds are often ineffective in vivo due to the ability of Bp and Bm to survive and replicate intracellularly (34).

For the reasons noted above, there is a need in the art for additional small molecule inhibitors of intracellular *Burkholderia*, as well as new cell-based phenotypic screening methods for small molecule inhibitors of intracellular *Burkholderia* that are actively replicating and spreading in mammalian cells.

SUMMARY OF THE INVENTION

As noted above, *Burkholderia pseudomallei* (Bp) and *Burkholderia mallei* (Bm) are Tier-1 select agents that cause highly lethal human infections with limited therapeutic options. Intercellular spread is a hallmark of *Burkholderia* pathogenesis and its prominent ties to virulence make it an attractive therapeutic target. In view of this, we developed a cell-based phenotypic screen for small molecule inhibitors of intracellular *Burkholderia* that are actively replicating and spreading in mammalian cells. Our high-throughput (HT) assay comprehensively addresses the entire *Burkholderia* intercellular lifecycle, including the critical step of cell-cell fusion. This strategy identified a number of inhibitory compounds that disrupt cell-cell spread by Bp and/or Bm. We further describe the mechanistic characterization of two of our most potent inhibitors, which hold particular promise as novel therapeutic countermeasures against these Tier 1 select agent pathogens.

Briefly, using a novel high-throughput cell-based phenotypic assay, we screened ~220,000 small molecules for their ability to disrupt intercellular spread by *Burkholderia thailandensis*, a BSL-2 surrogate. 268 hits were identified, and cross-species validation found 32 hits that also disrupt intercellular spread by Bp and/or Bm (see, e.g. FIG. 8). Among these were a novel fluoroquinolone analog, which we named burkfloxacin (BFX), which potently inhibits growth of intracellular *Burkholderia*, and flucytosine (5-FC), an FDA-approved antifungal drug. We found that 5-FC inhibits *Burkholderia*-mediated membrane fusion by inhibiting the secretion activity of a type VI secretion system, T6SS-5, a critical virulence determinant and central requirement for membrane fusion and intercellular spread. Bacterial conversion of 5-FC to 5-fluorouracil and subsequently to fluorouridine monophosphate is required for potent and selective activity against intracellular bacteria. In a fulminant murine model of respiratory melioidosis, treatment with BFX or 5-FC was significantly more effective than ceftazidime, the current drug of choice, for improving survival and decreasing bacterial counts in major organs. Our results demonstrate the utility of cell-based phenotypic screening for select-agent drug discovery and warrant the advancement of BFX and 5-FC as therapeutics for melioidosis.

The invention disclosed herein has a number of embodiments. Embodiments of the invention include, for example, methods of inhibiting intercellular spreading of *Burkholderia pseudomallei* or *Burkholderia mallei* bacteria, the methods comprising contacting the *Burkholderia pseudomallei* or *Burkholderia mallei* bacteria with at least one compound/agent shown in FIG. 8, wherein the *Burkholderia pseudomallei* or *Burkholderia mallei* bacteria are contacted with amounts of agent(s) sufficient to inhibit intercellular spreading of the *Burkholderia pseudomallei* or *Burkholderia mallei* bacteria. In certain embodiments of the invention, concentrations of at least 1 μM, 5 μM or 10 μM of the agent comprises amounts of agent(s) sufficient to inhibit intercellular spreading of the *Burkholderia pseudomallei* or *Burkholderia mallei* bacteria.

In typical embodiments of the invention, the agent is disposed within a composition further comprising a pharmaceutically acceptable carrier selected from at least one of: a pH adjusting agent, a buffering agent, a tonicity adjusting agent, a wetting agent, an antioxidant, a viscosity-increasing agent or a preservative. In certain embodiment *Burkholderia pseudomallei* or *Burkholderia mallei* bacteria are contacted with an agent selected to have certain chemical characteristics, for example, a fluoroquinolone compound and/or an agent comprising a morpholine moiety. Optionally, the agent is a prodrug that is converted by *Burkholderia pseudomallei* or *Burkholderia mallei* into an agent having activity against these bacteria.

In some embodiments of the invention, the agent is contacted with the *Burkholderia pseudomallei* or *Burkholderia mallei* bacteria growing in vivo as part of a therapeutic regimen, for example for a patient diagnosed with melioidosis or glanders disease. In some embodiments of the invention, the patient is administered the agent at doses between 1 mg/kg/day and 250 mg/kg/day; and/or the agent is administered to the patient at least 1, 2 or 3 times/day for at least 4, 5, 6, or 7 days. In some embodiments of the invention, the agent inhibits intercellular spreading of *Burkholderia pseudomallei* or *Burkholderia mallei* bacteria to an extent greater than that observed with ceftazidime at concentrations of 0.125 μM to 8 μM.

Another embodiment of the invention is a composition of matter comprising at least one agent shown in FIG. 8. Typically, the composition further comprises a pharmaceutically acceptable carrier selected from at least one of: a pH adjusting agent, a buffering agent, a tonicity adjusting agent, a wetting agent, an antioxidant, a viscosity-increasing agent or a preservative. In some embodiments of the invention, the agent comprises a fluoroquinolone and/or a morpholine group. Optionally, the agent is a prodrug that is converted by *Burkholderia pseudomallei* or *Burkholderia mallei* into an agent having activity against said bacteria. In certain embodiments of the invention the composition further comprises at least one additional agent selected for its ability to inhibit growth of *Burkholderia pseudomallei* and/or *Burkholderia mallei* bacteria, such as a Flucytosine; a Trimethoprim; a Levofloxacin; a Flumequine; a Sulfamethoxazole; a Gatifloxacin; a Perfloxacin; an Oxolinic acid; a Monensin; a Ceftazidime; a carbapenem; an amoxicillin-clavulanic acid or an Artemisinin. Optionally the composition further comprises an excipient selected to facilitate parenteral administration to a patient diagnosed with melioidosis or glanders disease.

Yet another embodiment of the invention is a method of identifying an agent capable of disrupting intercellular spread of *Burkholderia* species; the method comprising placing mammalian cells infected with *Burkholderia thailandensis* bacteria (e.g. eGFP-expressing HEK293 cells) that are actively replicating and spreading in the mammalian cells into a plurality of containers; placing a plurality of test agents into the plurality of containers so that one agent is present in one container; allowing the *Burkholderia thailandensis* bacteria to grow for a period of time; imaging the relative abundance and size of bacterial plaques in the plurality of containers; and then identifying agents that inhibit plaque formation; such that agents capable of disrupting intercellular spread of *Burkholderia* species are identified. Typical embodiments of the invention further examining the ability of an agent identified as inhibiting *Burkholderia thailandensis* intercellular spreading to inhibit intercellular spreading of *Burkholderia pseudomallei* and/or *Burkholderia mallei*.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Figure 1:
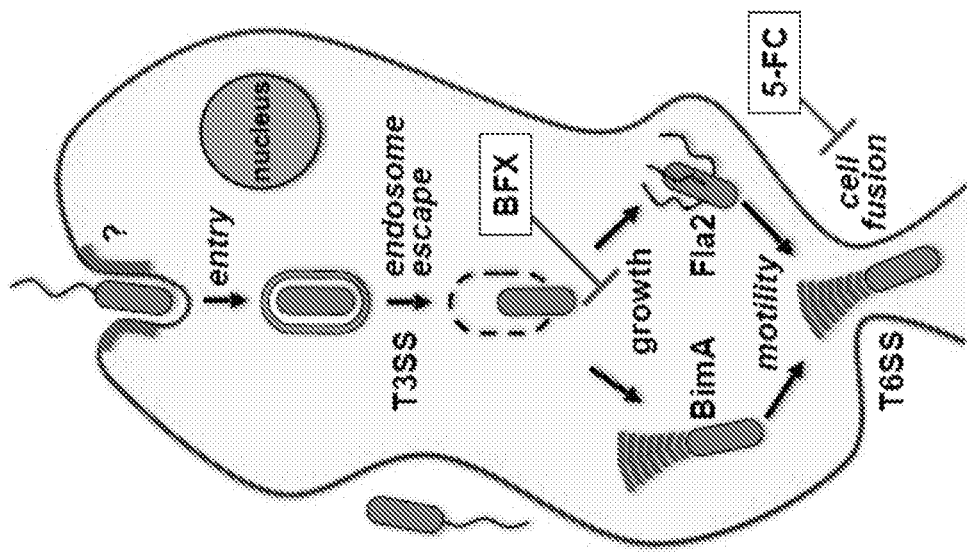
FIG. 1. The *Burkholderia* intercellular lifecycle, showing points of inhibition by two newly-discovered small molecule inhibitors, burkfloxacin (BFX) and flucytosine (5-FC). Diagram of the *Burkholderia* intercellular lifecycle, illustrating *Burkholderia*'s ability to invade, escape the endosome, locomote, replicate intracellularly, and fuse host cell membranes. Two priority compounds, BFX and 5-FC, were found to inhibit intracellular replication and membrane fusion, respectively.

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Embodiments of the invention include methods for identifying compounds capable of disrupting intercellular spread of *Burkholderia* species, compounds identified by these methods (see, e.g., FIG. 8), and methods for making and using these compounds.

For example, some embodiments of the invention include methods of identifying agents capable of disrupting intercellular spread of *Burkholderia* species. Typically, these methods comprise placing mammalian cells (e.g. eGFP-expressing HEK293 cells) infected with *Burkholderia thailandensis* bacteria that are actively replicating and spreading in the mammalian cells into a plurality of containers along with a plurality of test agents into so that one agent is present in one container. In these methods *Burkholderia thailandensis* bacteria are allowed to grow in the containers for a period of time (e.g. 18-22 hours) and then the relative abundance and/or size of bacterial plaques in the plurality of containers is observed. The methods can include the step of comparing the relative abundance and size of bacterial plaques in the plurality of containers to *Burkholderia thailandensis* bacteria growing in a control container (e.g. a container having no inhibitors). Using the methods disclosed herein, agents capable of disrupting intercellular spread of *Burkholderia* species are identified. In certain embodiments of the invention, the methods further comprise examining the ability of an agent that has been identified as inhibiting *Burkholderia thailandensis* intercellular spreading in this methodology to inhibit intercellular spreading of *Burkholderia pseudomallei* and/or *Burkholderia mallei* (e.g. where these *Burkholderia* species are used in a version of the described methodology rather than *Burkholderia thailandensis*). As disclosed in detail below, these methods have identified a number of agents capable of inhibiting intercellular spreading of *Burkholderia pseudomallei* and/or *Burkholderia mallei*.

Embodiments of the invention include compositions of matter comprising one or more compounds identified herein as disrupting intercellular spread by *Burkholderia* (see e.g., FIG. 8), for example a composition comprising Burkfloxacin as shown below:

In certain embodiments of the invention, an inhibitory agent such as Burkfloxacin is disposed within a composition further comprising a pharmaceutically acceptable carrier selected from at least one of: a pH adjusting agent, a buffering agent, a tonicity adjusting agent, a wetting agent, an antioxidant, a viscosity-increasing agent or a preservative. Optionally, these compositions comprise a plurality or "cocktail" of agents that inhibit intercellular growth of *Burkholderia pseudomallei* or *Burkholderia mallei* bacteria. Illustrative agents in addition to Burkfloxacin include, for example, Flucytosine; Trimethoprim; Levofloxacin; Flumequine; Sulfamethoxazole; Gatifloxacin; Pefloxacin; Oxolinic acid; Monensin; Ceftazidime; Doxycycline, a carbapenem; amoxicillin-clavulanic acid (coamoxiclav); or Artemisinin. In certain embodiments of the invention, the compositions comprise an excipient selected to facilitate oral, or alternatively parenteral, administration of the agent to a patient diagnosed with melioidosis or glanders disease.

Embodiments of the invention further comprise methods of making these compositions, for example by formulating and/or combining various composition constituents disclosed herein using art accepted practices (see, e.g., the Examples below and the HANDBOOK OF PHARMACEUTICAL MANUFACTURING FORMULATIONS by Sarfaraz K. Niazi). Related embodiments of the invention include use of at least one agent shown in FIG. 8 as described herein in the manufacture of a medicament for the treatment of a disease or condition characterized by the infection with *Burkholderia pseudomallei* or *Burkholderia mallei* bacteria, in a subject in need thereof (e.g. a patient diagnosed with melioidosis or glanders disease). Optionally in this use, at least one additional agent selected for its ability to inhibit growth of *Burkholderia pseudomallei* and/or *Burkholderia mallei* bacteria is used in addition to one agent shown in FIG. 8 in the manufacture of a medicament for the treatment of a disease or condition characterized by the infection with *Burkholderia pseudomallei* or *Burkholderia mallei* bacteria, in a subject in need thereof.

Figure 8:
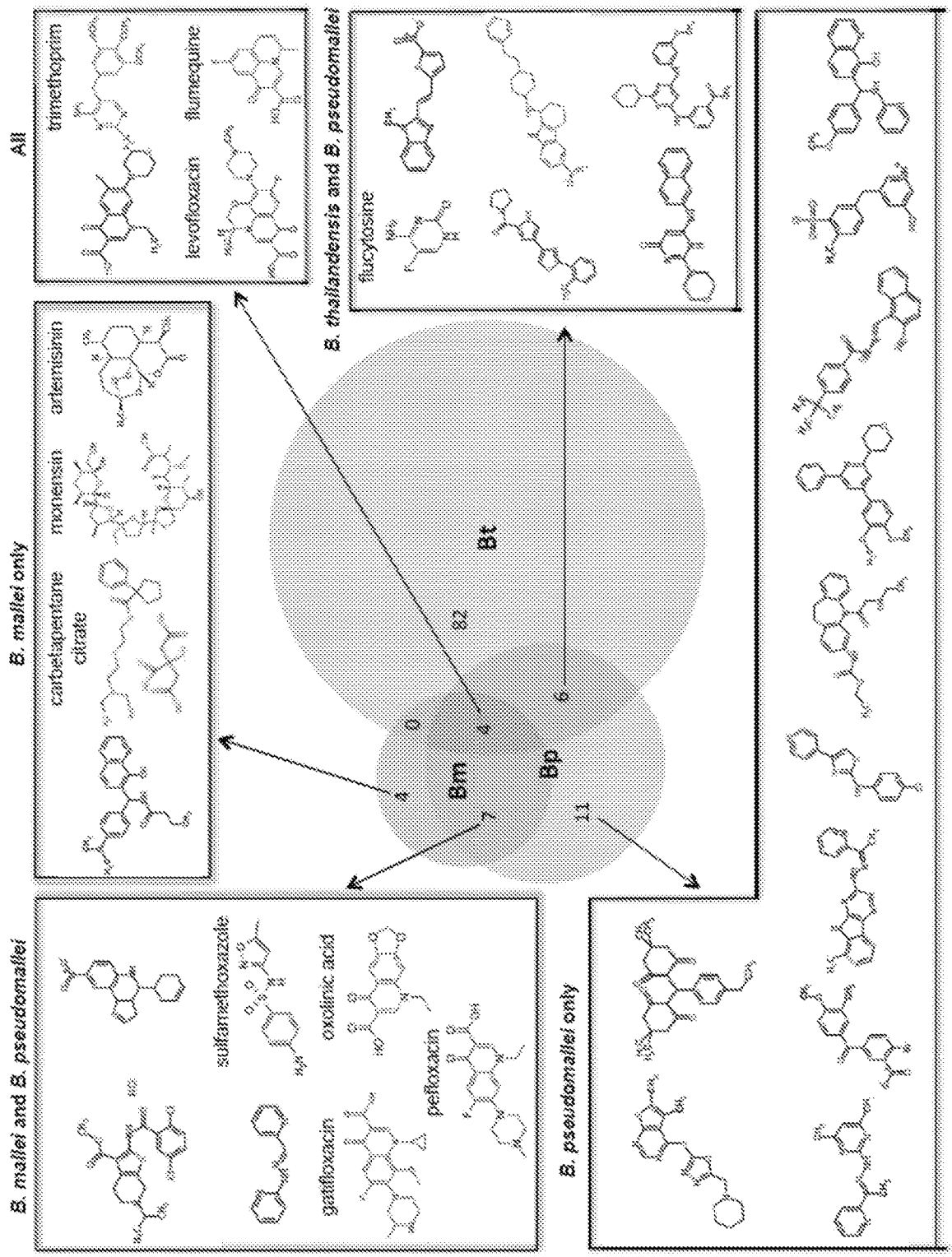
FIG. 8. A schematic including chemical structures of 32 compounds identified as reproducibly inhibiting intercellular spread by *Burkholderia pseudomallei* and/or *Burkholderia mallei* bacteria. In this figure, the 32 compounds are organized by their efficacy against Bp, Bm, Bt, or combinations thereof. Interestingly, morpholine ring moieties were common among agents identified as inhibiting intercellular spread by *Burkholderia pseudomallei* and/or *Burkholderia mallei* bacteria. Morpholine rings are present in many pharmaceutical products, including the antibiotic linezolid. Without being bound by a specific theory or mechanism of action, it is believed that morpholine rings confer added potency against intracellular pathogens by facilitating entry into mammalian cells harboring pathogens, including *Burkholderia pseudomallei* and *Burkholderia mallei*.
Figure 9:
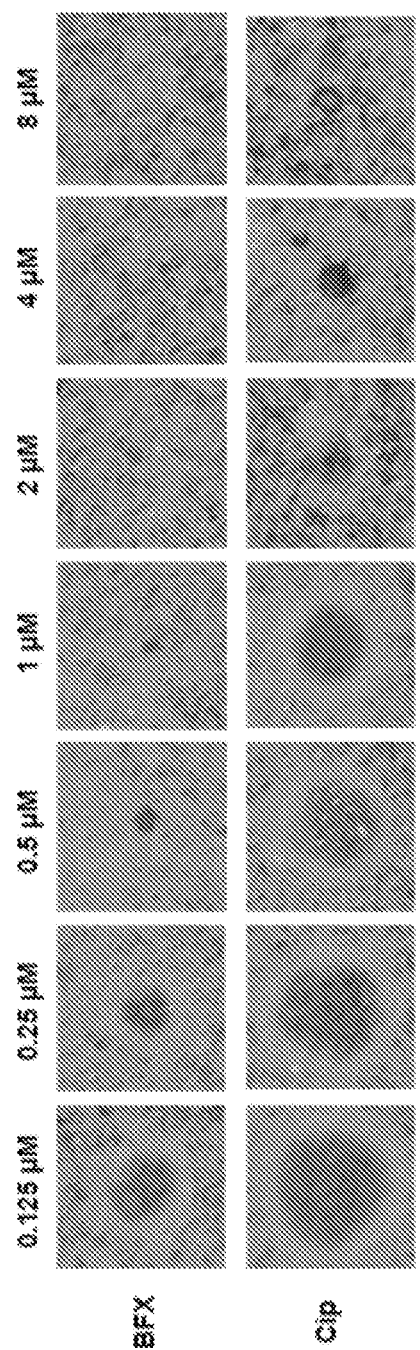
FIG. 9. BFX is a more potent inhibitor of intercellular spread by *Burkholderia thailandensis* than Cip. Images show multinucleate cell (MNC) formation 18 hours of infection, in the presence of BFX or Cip at concentrations ranging from (0.125 µM to 8 µM). BFX prevents plaque formation at 8-fold lower concentrations than Cip, despite the fact that the two compounds have comparable in vitro MICs (1.3 µg/ml for Cip and 2.6 µg/ml for BFX). This suggests that the superior efficacy of BFX is a result of more efficient intracellular accumulation, rather than higher bactericidal/bacteriostatic activity.
Figure 10:
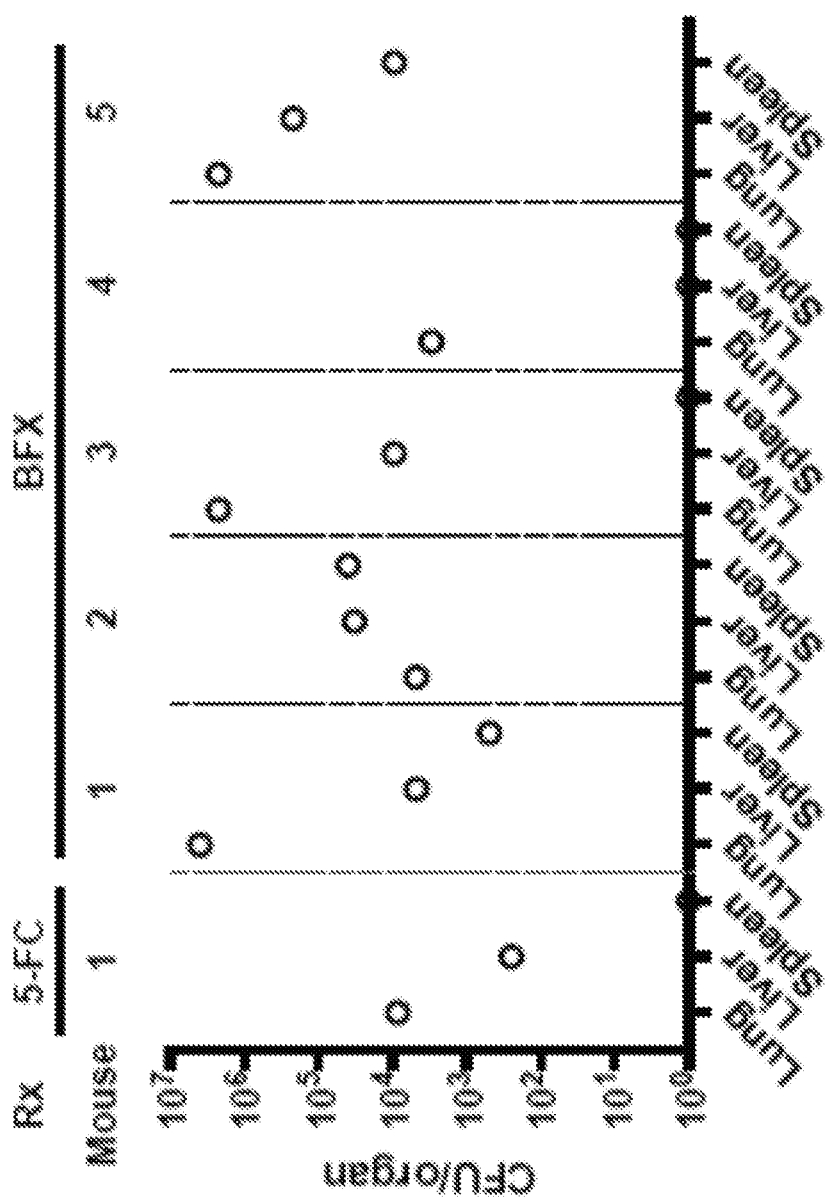
FIG. 10. Bacterial loads in the lungs, liver and spleen of mice surviving the entire study duration (10 days) following *B. pseudomallei* infection. For almost all mice surviving until day 10 post-infection (1 5-FC treated and 5 BFX treated), bacterial loads in the liver and spleen were significantly lower than in the lung. This suggests that 5-FC and BFX's may reduce mortality by abrogating bacterial dissemination from the lung.

Embodiments of the invention also include methods of inhibiting intercellular spreading of *Burkholderia pseudomallei* or *Burkholderia mallei* bacteria. These methods comprise, for example, contacting the *Burkholderia pseudomallei* or *Burkholderia mallei* bacteria with at least one inhibitory agent disclosed herein, for example an agent selected from Burkfloxacin; Flucytosine; Trimethoprim; Levofloxacin; Flumequine; Sulfamethoxazole; Gatifloxacin; Pefloxacin; Oxolinic acid; Monensin; and/or Artemisinin. In these methods, the *Burkholderia pseudomallei* or *Burkholderia mallei* bacteria are contacted with amounts of agent(s) sufficient to inhibit intercellular spreading of the *Burkholderia pseudomallei* or *Burkholderia mallei* bacteria. In embodiments of the invention, concentrations of 10 μM of an agent shown in FIG. 8 are observed to comprise amounts of agent(s) sufficient to inhibit intercellular spreading of the *Burkholderia pseudomallei* or *Burkholderia mallei* bacteria. In this context, embodiments of the invention include, for example, compositions comprising an agent shown in FIG. 8 (e.g. at a concentration of at least 10 μM, or 1 μM or 0.1 μM) in combination with a *Burkholderia thailandensis*, *Burkholderia pseudomallei* or *Burkholderia mallei* bacteria.

In some methods of inhibiting intercellular spreading of *Burkholderia pseudomallei* or *Burkholderia mallei*, the agent is disposed within a composition further comprising a pharmaceutically acceptable carrier selected from at least one of: a pH adjusting agent, a buffering agent, a tonicity adjusting agent, a wetting agent, an antioxidant, a viscosity-increasing agent or a preservative. Such pharmaceutically acceptable carriers are useful in embodiments of the invention where the agent is contacted with the *Burkholderia pseudomallei* or *Burkholderia mallei* bacteria growing in vivo, for example when the agent is administered to a patient diagnosed with melioidosis or glanders disease.

In certain embodiments of the invention, one or more compounds shown in FIG. 8 may be systemically administered, e.g., in combination with a pharmaceutically acceptable vehicle such as an inert diluent or other excipient. For compositions suitable for administration to humans, the term "excipient" is meant to include, but is not limited to, those ingredients described in Remington: The Science and Practice of Pharmacy (2 Volumes) 22nd Revised edition by Loyd V. Allen Jr (Editor), which is incorporated herein by reference. Such pharmaceutically acceptable vehicles are useful in embodiments of the invention where the agent is administered to a patient diagnosed with melioidosis or glanders disease.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York, which is incorporated herein by reference. For example, an, effective dose can be estimated initially either in cell culture assays or in suitable animal models such as the murine model disclosed in Example 6. Specifically, there are a number of mouse models of glanders and melioidosis that allow artisans to determine the appropriate concentration ranges and routes of administration of anti-infective agents such as those shown in FIG. 8 (see, e.g. Ulett et al., J Antimicrob Chemother. 2003 January; 51(1):77-81; Estes et al., Expert Rev Anti Infect Ther. 2010 March; 8(3): 325-338, and Barnes et al., Antimicrob Agents Chemother 61:e00082-17). Information from these models allows artisans to determine useful dose and route parameters for administration of such agents in humans. A therapeutic dose can also be selected by analogy to dosages for comparable therapeutic agents.

As noted above and illustrated in the working embodiments of the invention discussed below, using the disclosure provided herein, doses of agents useful in the treatment of conditions such as melioidosis or glanders disease can be determined using conventional means. For example, in embodiments of the invention using Burkfloxacin, a patient can be administered the agent at doses between 5 mg/kg/day and 30 mg/kg/day. In embodiments of the invention using Flucytosine, a patient can be administered the agent at doses between 50 mg/kg/day and 150 mg/kg/day. In embodiments of the invention, the agent can be administered to the patient according to conventional methods, such as for at least 1, 2 or 3 times/day, for at least 4, 5, 6, or 7 days.

The studies with animal models disclosed below provide working examples providing information on how effective in vivo doses are determined. Our studies and other embodiments and aspects of the invention are disclosed in the following sections.

EXAMPLES

Figure 2:
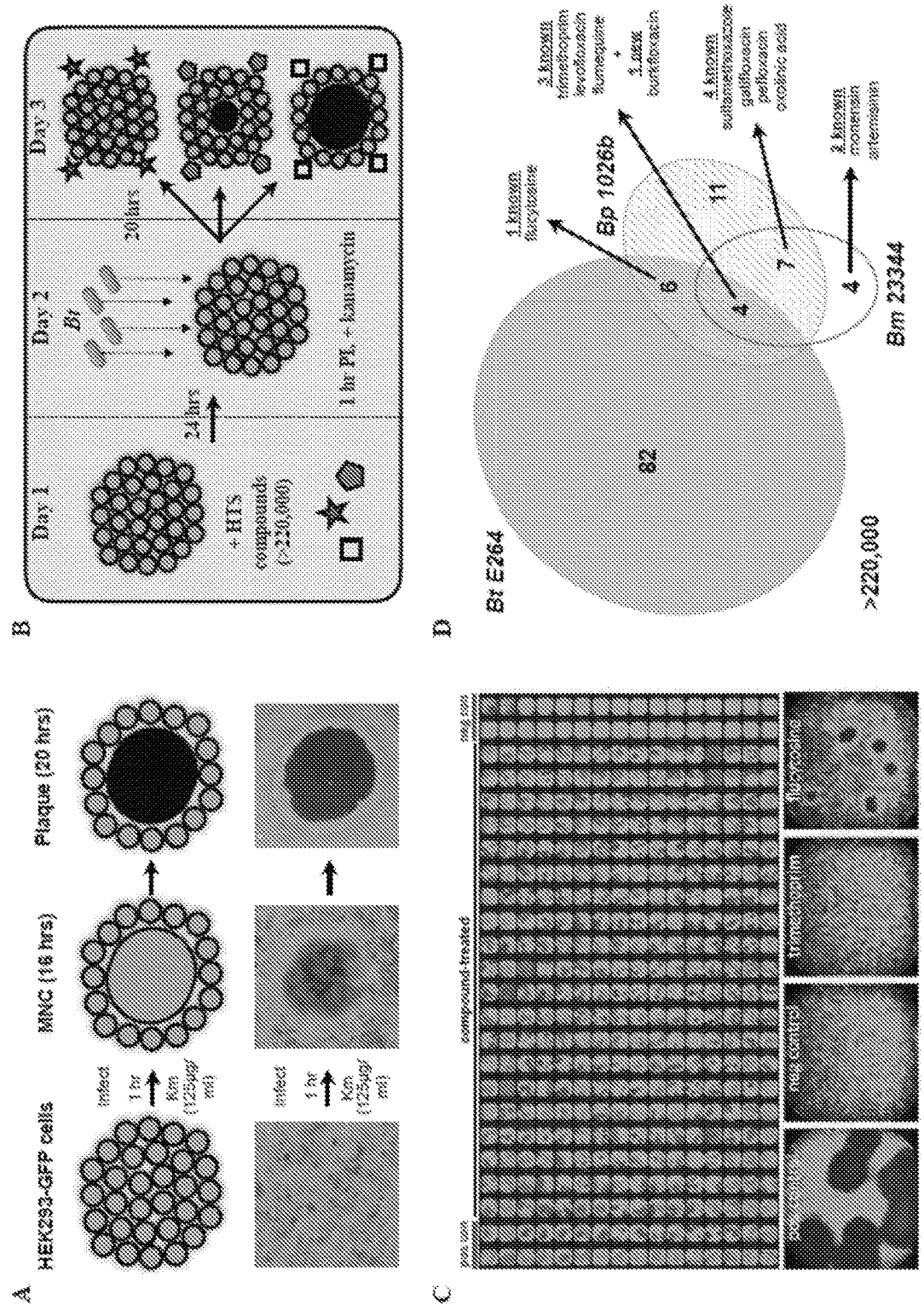
FIG. 2. High-throughput screening for small molecule inhibitors of *Burkholderia* intercellular spread. (A) Schematic of the cell fusion assay, with example well images. Cell monolayers are infected, treated with 125 μg/ml kanamycin after one hour to prevent extracellular growth, and incubated for 20 hours. (B) Schematic of the high-throughput phenotypic small molecule screen. Cells are seeded into 384-well plates and treated with small molecules, incubated for 24 hours, and then subjected to the cell fusion assay and evaluated for plaque formation. (C) Example 384-well plate image from screening of an FDA-approved drug library (Prestwick) at 5 µM concentration. The lower panel shows the enlarged image of a positive control well (DMSO-treated and infected), negative control well (uninfected), and wells treated with the known antibiotic trimethoprim and the FDA-approved antifungal 5-FC. (D) A proportional Venn diagram showing the number of small molecules that reproducibly inhibited intercellular spread by Bt, Bp, and Bm. Of the 268 primary hits originally identified during high-throughput screening against Bt, 92 reproducibly inhibited Bt intercellular spread ($\geq$80% of wells tested), and 32 reproducibly inhibited intercellular spread by Bp and/or Bm.
Figure 3:
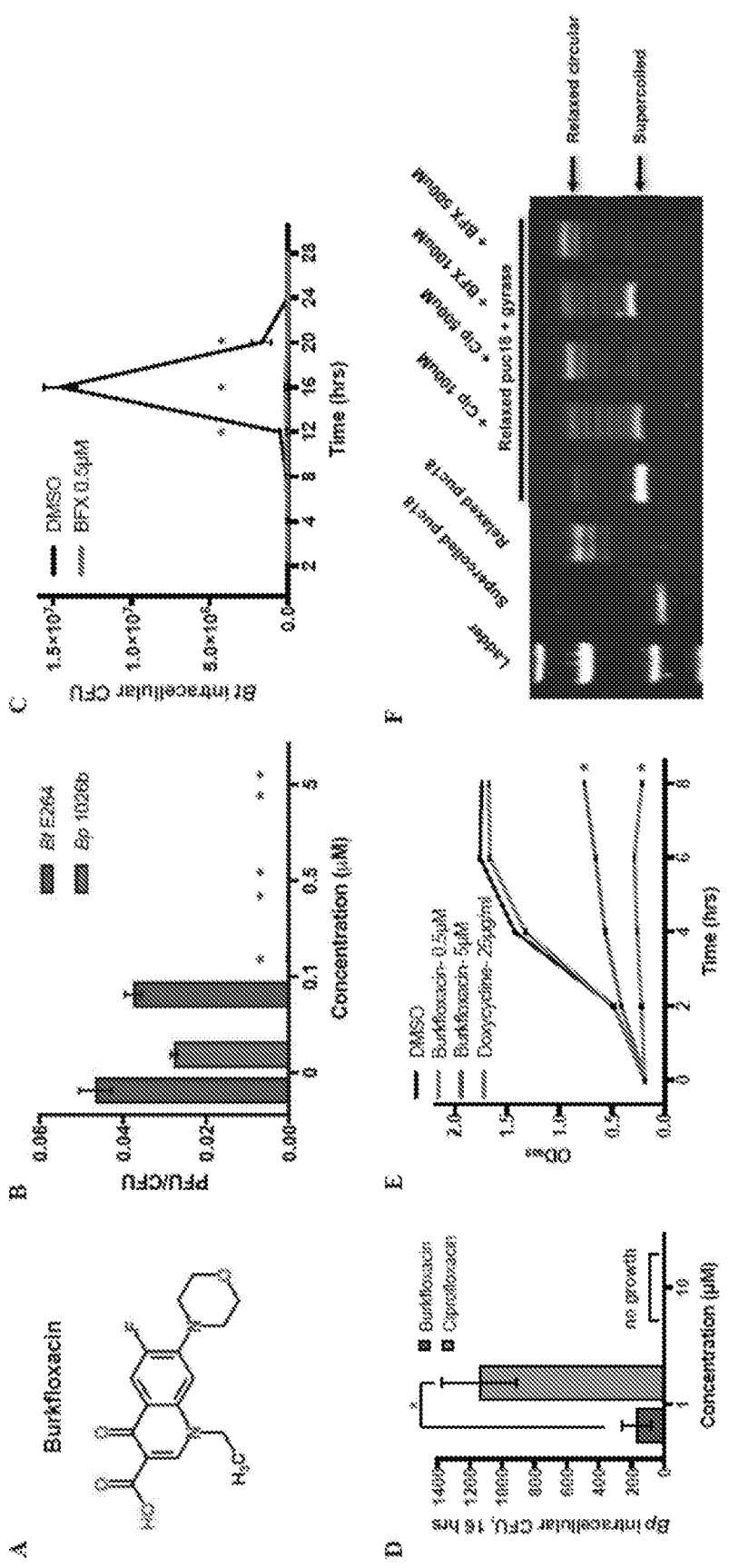
FIG. 3. Identification of a novel fluoroquinolone, BFX, as a potent inhibitor of Burkholderia intracellular replication. (A) Chemical structure of BFX (1-Ethyl-6-fluoro-7-(4-morpholinyl)-4-oxo-1,4-dihydro-3-quinolinecarboxylic acid). (B) BFX treatment results in near-complete inhibition of intercellular spread by Bt E264 and Bp 1026b at a concentration of 0.5 µM. Plaque forming efficiency was assessed by the number of plaque forming units (PFU) per CFU in HEK293 cells 16 hours after infection (*P<0.001). (C) BFX inhibits intracellular replication of Bt at a concentration of 0.5 µM, but not invasion. Intracellular bacterial counts were similar at 2 hours (P=0.5) but significantly lower in BFX-treated cells at 12, 16, and 20 hours after infection (*P<0.05). (D) At a concentration of 1 µM, seven-fold fewer CFU were recovered from BFX-treated cells vs Cip-treated cells at maximal intracellular growth (16 hrs post-infection) [*P<0.05]. (E) BFX does not inhibit in vitro growth of Bt at a concentration that robustly inhibits intracellular replication (0.5 µM), but does at 10-fold higher concentration (5 µM), suggesting accumulation of burkfloxacin inside host cells (*P<0.001). (F) BFX inhibits the negative supercoiling activity of E. coli DNA gyrase, similarly to Cip. All error bars represent the SEM.
Figure 4:
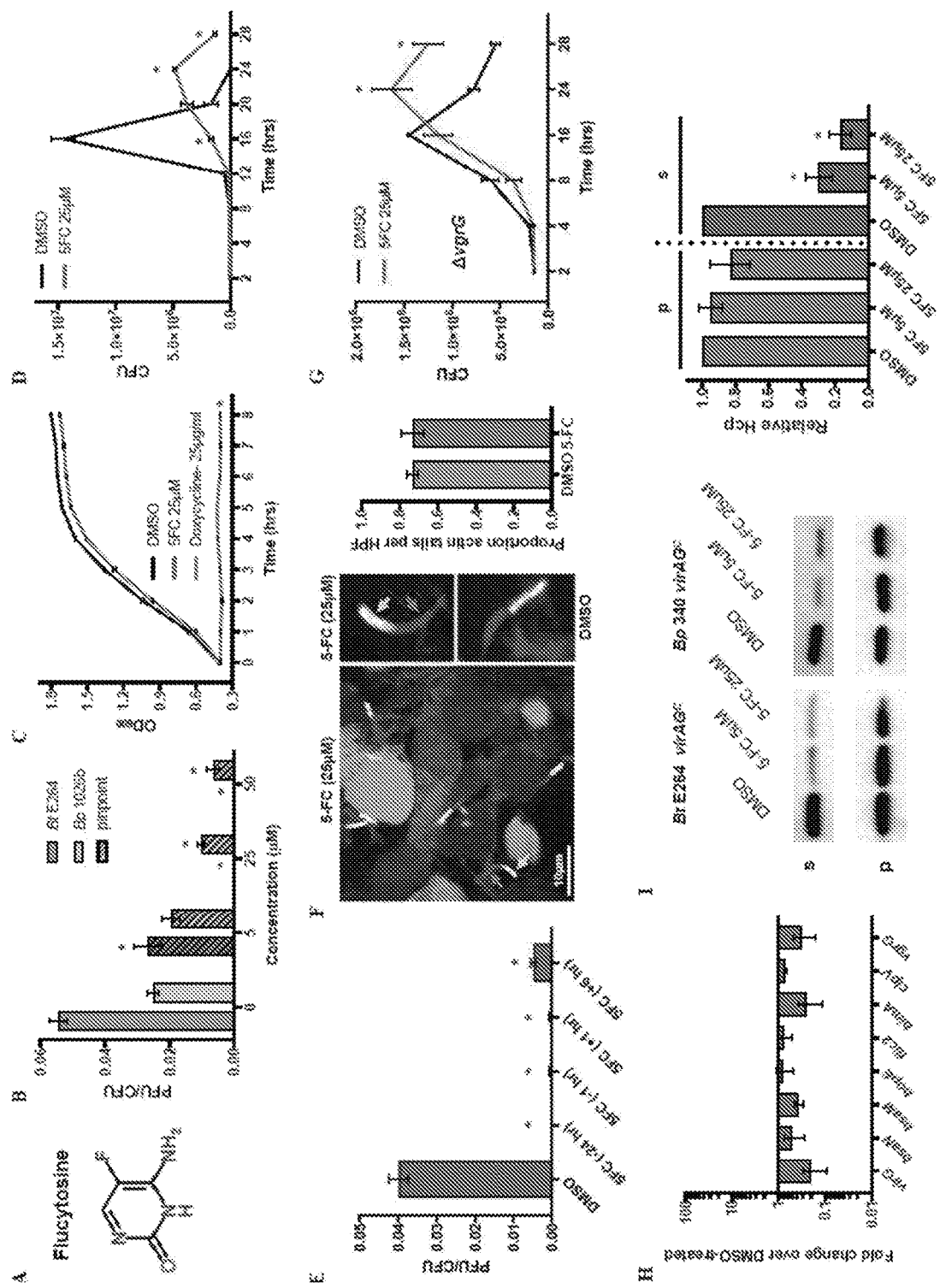
FIG. 4. The FDA-approved antifungal 5-FC potently inhibits Burkholderia intercellular spread by disrupting the secretion activity of the Type 6 Secretion System-5 (T6SS-5). (A) Chemical structure of 5-FC. (B) Plaque forming efficiency of Bt E264 and Bp 1026b at increasing concentrations of 5-FC. 5-FC completely inhibits plaque formation by Bt at a concentration of 25 µM. Striped bars indicate that plaques were pinpoint in size (*P<0.01). (C) 5-FC delays and decreases, but does not eliminate, intracellular replication of Bt (*P<0.05). (D) 5-FC does not significantly inhibit in vitro growth at a concentration that robustly inhibits intercellular spread (25 µM) [*P<0.001] (E) 5-FC robustly inhibits intercellular spread irrespective of time of addition (24 hrs prior to infection, 1 hr prior, 1 hr after, and 6 hrs after), suggesting that 5-FC blocks a late lifecycle step downstream of endosome escape (replication, motility, or membrane fusion) [*P<0.001]. (F) Fluorescence microscopy demonstrates that 5-FC does not inhibit actin-mediated intracellular motility (actin=blue (indicated by purple arrow), Bt=white (indicated by yellow arrow), HEK293 GFP and RFP-expressing cells=red and green). Equal proportions of DMSO and 5-FC-treated intracellular Bt express actin tails at 9 hours after infection. HPF=high powered field. (G) 5-FC does not inhibit the intracellular replication of a fusion defective mutant ($\Delta$vgrG), suggesting that it inhibits membrane fusion (*P<0.05). (H) 5-FC does not significantly alter expression of virulence loci inside cells, including those belonging to the T6SS-5 (clpV5, the T6SS-5 AAA-ATPase, and vgrG5, the T6SS-5 apparatus tip component), T3 $SS_{Bsa}$ (bsaM, an apparatus component, and bopE, a secreted effector with guanine nucleotide exchange (GEF) activity (39)), intracellular motility (bimA, an actin-nucleating factor required for intracellular motility (40), and fliC2, the flagellin component of the Fla2 flagellar system (24)), and virulence regulatory loci (virG and bsaN). (I) 5-FC inhibits secretion of Hcp (supernatant) in both Bt E264 and Bp 1026b (*P<0.05), but does not affect expression of Hcp (pellet), suggesting that 5-FC inhibits T6SS-5 secretion activity. All error bars represent the SEM.

Example 1: A High-Throughput Phenotypic Screen Identifies Small Molecule Inhibitors of *Burkholderia* Intercellular Spread The cell fusion assay in FIG. 2A was adapted for high-throughput screening by seeding eGFP-expressing HEK293 cells into 384-well plates pinned with a library of small molecules, infecting cells with *Burkholderia*, and imaging 18-22 hours later using laser scanning cytometry to assess the relative abundance and size of plaques (FIG. 2B, 2C).

Given that the readout is the result of cell fusion mediated by intracellular bacteria, the assay is capable of identifying compounds that inhibit any step of the intracellular infection pathway, have relatively low toxicity against mammalian cells, and are capable of penetrating both the host cell plasma membrane and the Gram-negative cell envelope.

Figure 5:
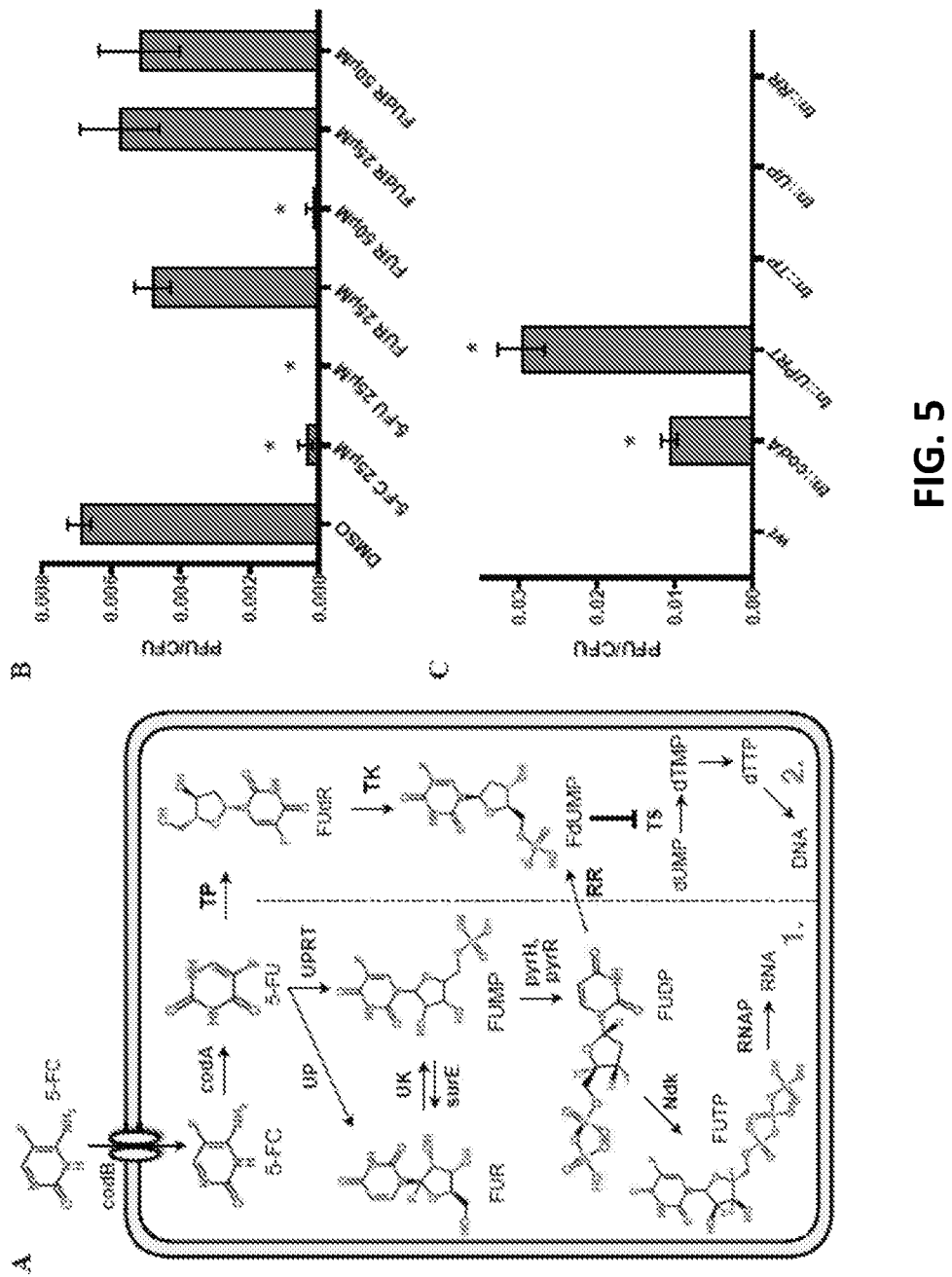
FIG. 5. The activity of 5-FC requires metabolic conversion to 5-fluorouracil (5-FU) and then to fluorouridine monophosphate (F-UMP). (A) Diagram of 5-FC metabolism in Burkholderia. 5-FC is metabolized by the pyrimidine salvage pathway. The pathway bifurcates into pathways 1 and 2, which provide nucleotide triphosphate (NTP) and dNTP anabolism and ultimately affect RNA and DNA synthesis, respectively. (B) Plaque forming efficiency of Bt in the presence of 5-FC and its downstream metabolites. Intercellular spread is inhibited by 5-FC, 5-FU, and at high concentrations, F-UR, but not by F-UdR (*P<0.05). (C) Transposon insertion into codA or uprt, but not TP, UP, or RR, results in resistance to 5-FC (*P<0.01), indicating that metabolism of 5-FC to 5-FU, and then to F-UMP, is essential for its inhibitory effect on Burkholderia.
Figure 6:
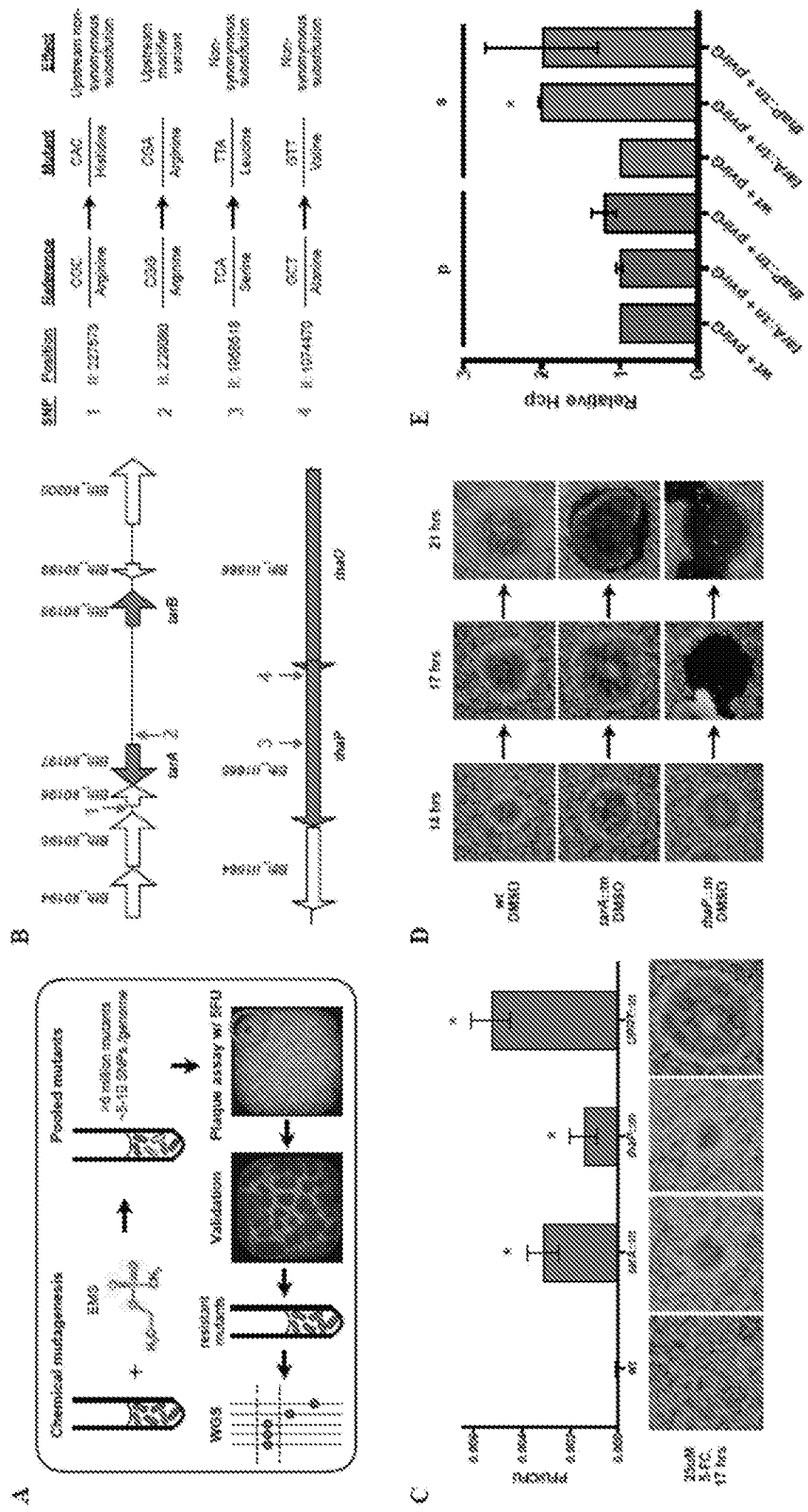
FIG. 6. 5-FC resistance screen identifies a novel regulator of T6SS-5 secretion activity. (A) Schematic of the forward genetic screen for 5-FC-resistant chemical mutants. WT Bt was mutagenized with ethyl methanesulfonate (EMS) and pooled mutants were used to infect cell monolayers in 384-well plates treated with 5-FU. MNCs were lysed and plated, and colonies were validated for resistance and subsequently whole-genome sequenced. (B) Mutations clustered in two genomic regions: a putative two-component transcriptional regulator (tarA and tarB) and a polyketide synthase cluster (thaP and thaO). Red arrows indicate the location of SNPs in resistant chemical mutants. SNPs conferring resistance were found to be a modifying mutation in the upstream region of tarA, a missense mutation upstream of the adjacent hypothetical protein Bth_II0196, and two missense mutations in thaP (see right panel for SNP details). (C) Disruptive transposon insertions into tarA and thaP result in partial resistance to 5-FC. Tn insertion into tarB and thaO also resulted in partial resistance. Transposon insertion into UPRT, for comparison, results in full resistance (*P<0.05). (D) tarA and thaP mutants display accelerated plaque formation relative to wt, in the absence of compound. (E) The tarA mutant with a plasmid expressing VirG (pVirG) has consistently elevated Hcp secretion (supernatant) but similar Hcp expression (pellet), relative to wt with pVirG, suggesting that tarA negatively regulates T6SS-5 secretion activity (*P<0.01). The thaP mutant also displayed increased Hcp secretion, but this effect was not as consistent. All error bars represent the SEM.
Figure 7:
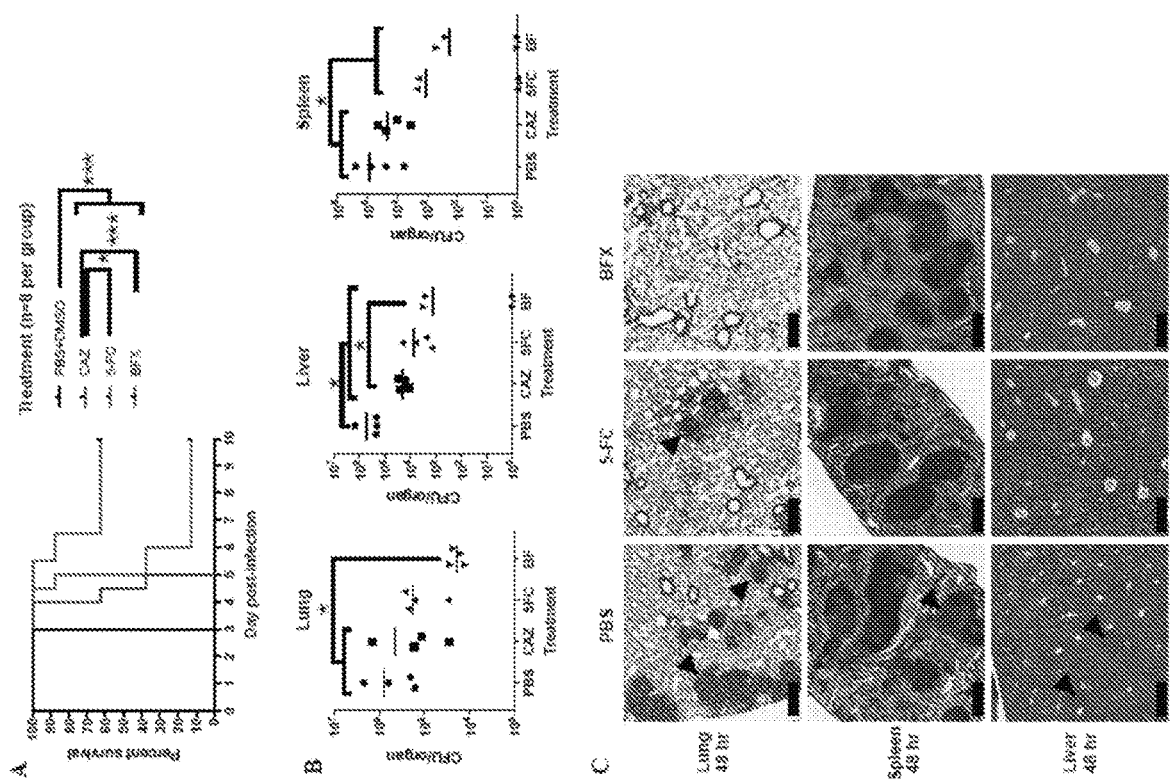
FIG. 7. 5-FC and BFX suppress B. pseudomallei virulence in vivo. (A) Treatment with 5-FC and BFX improved survival in a lethal mouse model of melioidosis and outperformed ceftazidime treatment, the current therapy of choice (***P<0.001; *P<0.05). (B) 5-FC and BFX decreased bacterial loads in the lungs, liver and spleens of mice infected with B. pseudomallei (*P<0.05). Bacterial burden was measured 48 hours after infection. (C) 5-FC and BFX reduced inflammation and necrosis in the lung, spleen, and liver tissue of infected mice. Shown are lung, spleen, and liver sections from PBS, 5-FC, and BFX-treated mice harvested 48 hours after infection. PBS-treated mouse lung tissue showed extensive interstitial, perivascular, and peribronchiolar inflammation (black arrows). Inflammation was less prominent and more focal in 5-FC-treated mouse lungs (black arrow) and was undetectable in BFX-treated lungs. Splenic tissue from PBS-treated mice showed large areas of mononuclear infiltration (black arrow) and necrosis (blue arrow) within red and white pulp, whereas spleens from 5-FC and BFX-treated mice were largely spared. Liver tissue from PBS-treated mice showed significant periductal mononuclear infiltration (black arrows), which was reduced in 5-FC-treated mice and undetectable in BFX-treated mice. Scale bars represent 300 µm. All error bars represent the SEM.

A curated small molecule library was screened for activity against intracellular Bt strain E264 utilizing the facilities of the UCLA Molecular Screening Shared Resource. FIG. 2C shows a pilot screen using an FDA-approved sub-library, demonstrating the ability to identify known (trimethoprim) and new (flucytosine) inhibitors (FIG. 2C). Screening efforts were then scaled to accommodate >220,000 compounds. Over the course of the screen, control wells yielded negligible false-positive (0%) and false negative (0.0091%) hit rates (FIG. 2C). An initial set of 268 compounds was found to abrogate plaque formation by Bt E264, yielding a conservative primary hit rate of 0.0012. Validation was conducted in multiplicate using Bt E264, Bp 1026b (Asian clinical isolate), and Bm 23344 (human isolate), resulting in 114 validated compounds that were binned according to species activity (FIG. 2D). Of these, four compounds, including three known antibiotics and one novel molecule which we named burkfloxacin (BFX), were found to consistently inhibit plaque formation by all three organisms. Seven compounds, including four known antibiotics, inhibited plaque formation by Bm and Bp, and four compounds were specific for Bm only, including monensin and the antimalarial drug artemisinin. Flucytosine (5-FC), an FDA-approved antimycotic, was identified among the hits with activity against Bp and Bt, but not Bm. Of note, BFX and 5-FC were also tested against Bp MSHR305, an Australian clinical isolate, and were both effective at ablating plaque formation at a concentration of 5 μM. Following validation of activity against intracellular *Burkholderia*, cytotoxicity was assessed in HEK293 cells using an ATP-depletion cell viability assay. Both BFX and 5-FC had no effect on cell viability at concentrations 10-fold higher than the $IC_{100}$ (Table 1) and were prioritized for follow-up studies.

Example 2: BFX Potently Inhibits Growth of Intracellular *Burkholderia*

BFX is a synthetic morpholinated fluoroquinolone analog (FIG. 3A) that results in near-complete inhibition of plaque formation by Bt and Bp at a concentration of 0.5 μM (FIG. 3B). When compared with ciprofloxacin (Cip), BFX inhibited plaque formation by Bt at 8-fold lower concentrations (FIG. 9). We attribute the effectiveness of BFX to its ability to potently ablate growth of intracellular bacteria following entry (FIG. 3C). At a concentration of 1.0 μM, BFX resulted in a 7-fold reduction in bacterial cfu compared to Cip at the same concentration (FIG. 3D). Interestingly, significantly higher doses of BFX (5 μM) were needed to inhibit growth in laboratory medium (FIG. 3E), suggesting that accumulation occurs inside mammalian cells. This has been observed with other fluoroquinolones (35). We confirmed that BFX, like Cip, functions as a canonical fluoroquinolone (FIG. 3F), by demonstrating its ability to inhibit the negative DNA supercoiling activity of *Escherichia coli* DNA gyrase. We next evaluated BFX's activity against other gram-negative and gram-positive pathogens, and found that BFX is inhibitory for the growth of *E. coli* ATCC 25922 and *Pseudomonas aeruginosa* ATCC 27853, but not *Staphylococcus aureus* ATCC 29213 or fluoroquinolone-resistant clinical isolates of *E. coli* and *P. aeruginosa* (Table 2). In *Pseudomallei*-group species, fluoroquinolone resistance is primarily mediated by the BpeEF-OprC efflux system (20, 36). Comparing the MICs for BFX among BpeEF-OprC-positive and -negative Bp strains shows that BFX is similarly prone to efflux by this system (Table 3).

Example 3: The FDA-Approved Antifungal 5-FC Inhibits Intercellular Spread and Affects Activity of T6SS-5

Our screen also identified 5-FC, an FDA-approved antimycotic, as an inhibitor of plaque formation by Bt and Bp. 5-FC is a fluorinated cytosine analog (FIG. 4A) that serves as a first-line therapy for serious fungal infections, such as cryptococcal meningitis (37), and is included in the World Health Organization (WHO)'s List of Essential Medicines (38). In light of its established efficacy as an antifungal agent, we investigated the mechanism of 5-FC in an alternative context, as an inhibitor of *Burkholderia* cell-cell spread. As shown in FIG. 4B, 5-FC inhibits plaque formation by Bt and Bp in a dose-dependent fashion. 5-FC does not affect growth of bacteria in laboratory medium at concentrations that eliminate plaque formation (FIG. 4C), analogous to BFX. Unlike BFX, however, 5-FC does not prevent the growth of intracellular bacteria at concentrations that inhibit plaque formation, although a slight (3-fold) decrease and delay in attaining peak bacterial numbers is observed (FIG. 4D). Plaque formation is inhibited whether 5-FC is added to cells before or during the infection time course (FIG. 4E), which suggests an effect on a late intracellular lifecycle event (FIG. 1), such as bacterial motility or cell-cell spread. The proportion of bacteria associated with actin protrusions is equivalent in treated and untreated cells (FIG. 4F), suggesting that 5-FC does not block motility or earlier events such as bacterial escape from endosomes into the cytosol. Cell fusion allows for expansion of the replicative niche, and accordingly, an increase in intracellular bacterial counts. Importantly, treatment with 5-FC did not markedly alter peak intracellular growth of a fusion-defective mutant (ΔvgrG) (FIG. 4G). These results suggest that the reduction of bacterial numbers observed following treatment with 5-FC (FIG. 4D) is more likely an indirect effect of inhibition of cell-cell spread, rather than a direct effect on replication.

To further explore the mechanism, we investigated the effects of 5-FC on the expression of key virulence genes known to facilitate intracellular survival and cell-cell spread (39). Quantitative RT-PCR was performed on RNA from cells infected with Bt E264 in the presence and absence of 5-FC. With treatment, we found a modest (≤4-fold) reduction in the expression of virG, bsaM, bimA, and vgrG and no significant effect on other loci (FIG. 4H), which seemed insufficient to account for the near complete elimination of plaque formation that we observe. Accordingly, we investigated whether 5-FC has an effect on the functionality of T6SS-5. Using Western Blot, we observed a significant decrease in the quantity of Hcp5, the T6SS-5 inter-tubule subunit protein, secreted into culture supernatants by Bt and Bp following 5-FC treatment (FIG. 4I). The production of Hcp5 was not significantly affected by 5-FC, as demonstrated by equivalent signal intensities in the cell pellet fractions of treated and untreated bacteria (FIG. 4I). These results are consistent with an inhibitory effect of 5-FC on cell-cell spread via abrogation of T6SS-5 secretion activity.

Example 4: 5-FC Inhibition of Cell-Cell Spread Depends on Activity of Metabolic Intermediates The antifungal properties of 5-FC arise due to the cytotoxicity of its metabolic products (37, 40). As shown in FIG.

5A, following uptake of 5-FC by cytosine permease (CodB) and conversion to 5-FU by cytosine deaminase (CodA), the metabolism of 5-FC bifurcates into two pathways which ultimately result in antifungal activity via inhibition of RNA and DNA synthesis. However, while the orthologous pathways and enzymes are present in *Pseudomallei*-group *Burkholderia* (FIG. 5A), bacterial growth is mostly unaffected (FIG. 4D), implicating a unique mechanism for 5-FC in the inhibition of cell-cell spread. Accordingly, we investigated key 5-FC metabolic enzymes and their products for plaque formation phenotypes.

As shown in FIG. 5A, pathway 1 is involved in the synthesis of pyrimidine nucleotide triphosphates. We found that 25 μM 5-fluorouracil (5-FU), like 5-FC, completely abolished plaque formation (FIG. 5B). Fluorouridine (F-UR), a shunt intermediate between 5-FU and fluorouridine monophosphate (F-UMP), was minimally inhibitory at 25 μM, but fully inhibitory at 50 μM, suggesting a role for pathway 1 (FIG. 5A) in the inhibition of cell-cell spread. This is consistent with a lack of inhibitory activity by fluorodeoxyuridine (F-UdR), a pathway 2 intermediate, at concentrations up to 50 μM. We next investigated metabolic gene loci for roles crucial to the activity of 5-FC (FIG. 5C). We found that transposon insertion mutants in loci encoding codA (codA::tn) or uracil phosphoribosyltransferase (uprt::tn), obtained from an arrayed Bt transposon mutant library (41), were resistant to 5-FC, while mutants defective in thymidine phosphorylase uracil phosphorylase (up::tn), or ribonucleotide reductase (rr:tn) did not confer resistance, suggesting that the corresponding 5-FC metabolites (F-UdR, F-UR, F-dUMP, respectively) are not active against *Burkholderia* intercellular spread. Metabolic conversion to 5-FU and then to F-UMP are critical for the activity of 5-FC, and the results of our combined chemical and genetic approach suggest that F-UMP may be the active metabolite affecting T6SS-5-mediated cell fusion and spread.

Example 5: Chemical Mutagenesis Screen for 5-FC Resistance Identifies a Novel Regulator of T6SS-5 Activity To gain further insight into the inhibitory mechanism of 5-FC, we performed a forward genetic screen to identify mutations leading to resistance. WT Bt was treated with the DNA alkylating agent ethyl methanesulfonate (EMS). Pooled mutagenized bacteria were then used to infect cells in the presence of 25 μM 5-FU (FIG. 6A). The use of 5-FU instead of 5-FC eliminated selection for mutations in the enzyme CodA. MNCs were picked from 384-wells at 16 hours post-infection, lysed with detergent, and plated on L-agar for isolation of individual bacterial colonies. Resistant phenotypes were validated by cell infection assays in the presence of 5-FU. The uprt gene was PCR amplified and sequenced for all resistant mutants, and mutants containing single nucleotide polymorphisms (SNP) in this gene were eliminated. In total, approximately 6 million chemical mutants were assessed for resistance, of which 20 (0.0003%) demonstrated reproducible resistance to 5-FU. 13 (65%) of these resistant mutants had mutations in uprt and were discarded. No mutations were identified in the downstream metabolic enzymes, pyrH or ndk. The final 7 resistant strains, and the WT strain, were subjected to whole genome sequencing (WGS). SNPs were clustered in two genomic regions containing a putative two-component regulatory system (Bth_II0197 and Bth_II0198), which we named T6SS-5 activity regulators A and B (tarA and tarB), and another within a polyketide synthase cluster (Bth_II1665 and Bth_II1666; thaP and thaO), which produces a compound named thailandamide that in Bt is thought to be involved in quorum sensing (42) (FIG. 6B). Tn insertion mutations in tarA, tarB, and thaP resulted in partial resistance to 5-FC (FIG. 6C), consistent with the chemical mutagenesis screen. Interestingly, 5-FC resistant mutants displayed accelerated MNC/plaque formation in the absence of 5-FC (FIG. 6D), supporting the role of tarA/B as a suppressor of T6SS-5-mediated cell fusion.

Given our finding that 5-FC affects T6SS-5 activity (FIG. 4I), secretion of Hcp was assessed for the resistant mutants. We found that T6SS-5-mediated secretion of Hcp5, but not Hcp5 expression, was consistently two-fold elevated in a tarA::tn mutant relative to WT (FIG. 6E). Increased secretion of Hcp5 was also observed for a thaP::tn mutant, although the result was less consistent. These results suggest that T6SS-5-mediated cell fusion may be part of a regulatory network involving quorum sensing, and that inhibition of cell-cell spread by 5-FC may be due to an effect on this pathway.

Example 6: BFX and 5-FC Abrogate *B. pseudomallei* Pathogenicity In Vivo

Given the effectiveness of BFX and 5-FC at abrogating *Burkholderia* cell-cell spread, we evaluated their therapeutic efficacy using an acute, fulminant mouse model of melioidosis. BALB/c mice were infected intranasally with 4500 CFU of Bp 1026b, and BFX (10 mg/kg/day) or 5-FC (100 mg/kg/day) were administered intraperitoneally twice daily, with the first doses administered five hours after infection. The outcomes were compared to administration of placebo (PBS+20% DMSO) or ceftazidime (130 mg/kg/day). All animals in the placebo group succumbed to infection within three days, and all ceftazidime-treated animals by five days. In contrast, all (100%) mice receiving BFX, and 3/8 (36.7%) mice treated with 5-FC survived to five days post-infection ($p<0.001$) (FIG. 7A). Moreover, 5/8 (63%) of BFX-treated and 1/8 (12%) 5-FC treated mice survived the entire study duration (10 days). Survival rates were inversely correlated with bacterial loads in major organs, and numbers of bacteria in the lungs, livers, and spleens of BFX-treated mice were decreased relative to placebo and ceftazidime-treated controls at 48 hours post-infection (FIG. 7B). Bacterial loads were also decreased, although to a lesser extent, in 5-FC-treated mice. Interestingly, the majority of surviving mice treated with 5-FC or BFX showed low or undetectable bacterial loads at 10 days in liver and spleen compared to lung, suggesting that dissemination from the lung to these organs might portend a poor outcome (FIG. 10). Histopathology of pulmonary, hepatic, and splenic tissue from mice sacrificed 48 hours after infection revealed significantly reduced inflammation in 5-FC-treated mice relative to PBS-treated, and nearly undetectable inflammation in organs of BFX-treated mice (FIG. 7C). In summary, BFX and 5-FC demonstrate superiority to ceftazidime in a fulminant mouse model of melioidosis, supporting their promise as new therapeutic countermeasures.

Example 7: Illustrative Materials and Methods

Study Design

Compounds in the UCLA MSSR library (www.mssr.ucla.edu) were plated and tested in vitro for the ability to inhibit intercellular spread with the identities and order of the compounds blinded to the experimenter. Two priority lead compounds, BFX and 5-FC, were assessed for therapeutic efficacy in vivo using a mouse model of melioidosis. Animals were randomly assigned to treatment groups. Efficacy in vivo was determined on the basis of mortality, organ bacterial loads, and histopathological findings. The sample size of animals for in vivo studies was determined using Lamorte's power calculations and was selected to minimize the number of animals needed to obtain a statistically significant result.

High-Throughput Screen

25 µL of cell culture media [Dulbecco's Modified Eagle's Medium (DMEM) 10% bovine growth serum (BGS)] was dispensed into black clear-bottom 384-well plates (E&K Scientific, EK-30091) using a multidrop reagent dispenser (Thermo Fischer Scientific). Small molecules were pinned into plates using a Biomek FX robot to achieve a final well concentration of 5 µM (250 nL of 10 mM DMSO solution). eGFP expressing HEK293 cells were seeded onto the 384-well plates for a final well volume of 50 µL and cell count of 35,000/well. Plates were incubated for 24 hours at 37° C., and then infected with Bt E264 at a multiplicity of infection (MOI) of 0.01. Validation with Bp 1026b or Bm 23344 was conducted similarly, except that infections and subsequent steps were performed in our BSL3 facility. Plates were gently centrifuged (200×g for 5 min) to allow bacterial attachment to cells, and incubated at 37° C. for 1 h. After 1 h, media containing kanamycin was added to the wells for a final well concentration of 125 μg/ml to kill extracellular bacteria. Plates were incubated for 18-22 hours, fixed with 4% paraformaldehyde (final well concentration), and imaged by laser scanning cytometry (Image Express XL plate reader). Well images were analyzed qualitatively for the presence or absence of MNCs/plaques or the reduced abundance or size of MNCs/plaques. Uninfected wells treated with DMSO and wells treated with DMSO and infected with the wt parental strain served as negative and positive controls, respectively.

Cell Culture, Infection, and Intercellular Lifecycle Assays

HEK293 (ATCC CRL-1573) cells were grown in DMEM+10% BGS and 5% $CO_2$. Prior to experiments, plate wells were incubated at room temperature for 30 minutes with a 1:30 dilution of Matrigel liquid (BD) in serum-free DMEM for improved adherence of cells. For infection studies, cells were seeded at $1.8\times10^6$ cells per well in 6-well plates or $7.2\times10^5$ cells per well in 12-well plates. Following addition of bacteria to wells, plates were gently centrifuged as described above. Cells were infected at an MOI of 1 for invasion and intracellular replication experiments and an MOI of $4\times10^{-4}$ for cell fusion assays. One hour after infection, extracellular bacteria were killed by the addition of 1,000 μg/ml Km. For invasion and intracellular replication experiments, infected cells were washed with Hank's, harvested with 0.25% trypsin, and lysed with 0.2% Triton X-100+20 mM MgSO4 and 50 μg/ml DNase I (to reduce lysate viscosity). Intracellular colony-forming units (CFUs) were enumerated by plating serial dilutions of the lysate at indicated time points. For cell fusion assays, cells were infected as described above, overlaid with 125 μg/ml Km, and imaged 18-22 hours later by fluorescence microscopy and examined for the formation of MNCs/plaques. Plaque forming efficiency was calculated as the number of MNCs or plaques (plaque forming units; PFU) over the number of colony forming units initially used for the infection (CFU), which was assessed by plating a dilution of the bacterial solution used for infection.

Chemical Mutagenesis and 5-FC Forward Genetic Screen

Wild-type Bt were grown to mid-exponential phase ($OD_{600}$~1), washed three times with PBS, resuspended in PBS+1% ethyl methanesulfonate (EMS) and shaken at 37° C. for 10-15 minutes. After EMS treatment, bacteria were washed three times with PBS, then resuspended in LB-NS and allowed to recover at 37° C. for 1 h. Pooled mutants were then used to infect eGFP-expressing HEK293 cells treated with 25 μM 5-FU in 384-well plate format at an MOI of 0.03. Plates were centrifuged at 200×g for 5 min and a 125 μg/ml Km overlay was added after 1 h After 16 hours of incubation at 37° C., plates were scanned by laser scanning cytometry. Wells with MNCs were trypsinized, cells were lysed with 0.2% Triton X-100+20 mM MgSO4 and 50 μg/ml DNase I, and dilutions were plated on LB-NS plates. 10 colonies from each plate were picked, grown in LB-NS, and used to infect 5FU-treated cell monolayers to validate their resistance. One validated resistant colony from each MNC was sent for sequencing of the uprt gene to rule out resistance due to an inactivating SNP in this enzyme. For resistant mutants without SNPs in uprt (7 total) and the parental wild-type strain, genomic DNA was extracted and whole genome sequenced.

Mouse Model of *B. pseudomallei* Infection

All Select Agent animal work was carried out in a CDC/USDA Tier 1 approved facility at the University of Florida following Tier 1 regulations. This study was approved by the Institutional Animal Care and Use Committee at the UF (protocol #: 201609601). Female BALB/c mice between 4 and 6 weeks of age were purchased from Charles River Laboratories (Wilmington, MA). Animals were housed in Allentown microisolator cages under pathogen-free conditions. Bp1026b was grown overnight to an $OD_{600}$ of ~1 and frozen in 20% glycerol aliquots overnight at −80° C. An aliquot of each was thawed and CFU enumerated by dilution plating on LB medium. The target inoculation of 4,500 CFU in 20 μl was achieved by thawing an aliquot and dilution in PBS immediately prior to challenge. Animals were anesthetized with a KX cocktail containing 87.5 mg/kg of ketamine (Patterson Veterinary) and 12.5 mg/kg xylazine (Alfa Aesar) of body weight. Once fully anesthetized, groups of 8 mice (n=8) were challenged with the 20 μl inoculum by pipetting into the nares of the mouse alternating nostrils until fully inhaled. Starting at five hours post-infection, mice were treated twice daily via intraperitoneal injection of 100 μL of PBS+20% DMSO (negative control), 65 mg/kg of ceftazidime in 100 μL PBS (positive control), 50 mg/kg of 5-FC in 100 μL PBS, or 5 mg/kg of BFX in 100 μL PBS+20% DMSO. Two daily 50 mg/kg doses of 5-FC corresponds to 100 mg/kg/day, which falls within the recommended dosage range for humans (infants <1 mo: 25-100 mg/kg/day; adults: 50-150 mg/kg/day) [https://www.drugs.com/dosage/flucytosine.html]. Two daily 5 mg/kg doses of BFX corresponds to 10 mg/kg/day, which falls within the recommended dosage range for Cip in humans (pediatric: 6-30 mg/kg/day; adult: 5.7-21.4 mg/kg/day, assuming adult weight of 70 kg) [https://www.drugs.com/dosage/ciprofloxacin.html]. Each treatment group contained 8 mice. Overall survival was followed over a 10-day period. Mice were euthanized at humane endpoints or when moribund. Mice surviving to the tenth day were euthanized, and lungs, spleens, and livers were excised, and homogenized in 5 ml of 1×PBS using a stomacher (Seward). Undiluted and diluted homogenate were plated on LB agar to determine organ bacterial loads. Colonies were positively identified as Bp by spot-testing with the latex agglutination test as previously described (50, 51). A separate pre-determined endpoint study was undertaken to determine organ bacterial loads at 48 hours post-infection. Four mice per treatment group were infected and treated as described above, and then humanely euthanized and processed for lung, spleen, and liver organ loads as described above. One additional mouse per treatment group was infected as described and processed for histopathological analysis of the lungs, liver, and spleen. For this, organs were excised, fixed in 10% formalin, and processed for paraffin embedding at the UF Molecular Pathology Core. 5 µM sections were obtained at regular intervals from the middle of each organ and stained with H&E and analyzed by microscopy.

Data Analysis

Figures and graphs were prepared using Graphpad Prism and Keynote. Statistical analyses were performed with Student's t test or ANOVA implemented in Graphpad Prism.

Ethics Statement

Animal research was conducted under a protocol approved by Institutional Animal Care and Use Committee (IACUC) at the University of Florida (protocol 201609601), in full compliance with the Animal Welfare Act and other federal regulations and statutes pertaining to animals. All in vivo experiments were performed in an ABSL-3 facility at the UF Communicore's accredited animal research facility, managed by UF Animal Care Services. Humane care and treatment protocols were conducted according to i) 9 CFR Parts 1-4 (U.S.C. 2131-2156), and ii) the "Guide for the Care and Use of Laboratory Animals," NIH Publication No. 86-23.

Select Agent Experiments

In vitro experiments with Bp and Bm were performed in a BSL-3 facility at UCLA. Personnel wore tyvek suits and powered air purifying respirators. The BSL3 facilities at UCLA and UF are registered with the CDC DSAT and approved for possession, use, and transfer of Bp and Bm (Tier-1 Select Agents) under entity registration numbers C20090508-0836 and A20150312-1681 for UCLA and UF, respectively.

Reagents

BFX was purchased from ChemBridge (San Diego, CA), and flucytosine was purchased from Selleckchem (Houston, TX). Dimethyl sulfoxide was used as solvent for high-throughput screening and follow-up studies. Hcp antibodies were provided by Mary Burtnick at the University of South Alabama (Mobile, AL). Bt transposon mutants were provided by Colin Manoil at the University of Washington (Seattle, WA).

Bacterial Strains and Mutant Construction

Bt E264, Bp 1026b, Bp340 (Bp 1026b Δ(amrRAB-oprA), and Bm 23344 were grown in LB medium without NaCl (LB-NS) or with NaCl (Bm23344). In-frame mutations were constructed using allelic exchange as described previously (24, 26). Strains constitutively expressing VirA and VirG were constructed by insertion of a mini-Tn7 transposon containing the virAG genes from Bp340 downstream of the S12 ribosomal subunit promoter, as described previously (26). Plasmid construction was performed using a derivative of the broad-host range plasmid pBBR1-MCS2 containing the nptt kanamycin resistance gene, as previously described (24, 26).

Small Molecule Library

The small molecule library housed at the UCLA molecular screening shared resource (MSSR) contains ~220,000 small molecules. Among these are 1,120 FDA-approved drugs (Prestwick library), 1,280 pharmacologically-active drug-like molecules (LOPAC collection), 8,000 molecules from the Microsource Spectrum Collection, 8,000 molecules which target kinases, protease, ion channels and GPCRs (druggable compound set), 20,000 compounds from a lead-like compound set, 30,000 compounds from the ChemBridge DiverSet E, 50,000 diverse molecules from Life Chemicals, 5,000 compounds from the UCLA in-house collection, and ~100,000 diverse molecules from libraries proprietary to the UCLA MSSR.

Cellular Toxicity Assay

HEK293 cell viability in the presence of small molecules was assessed using the CellTiter-Glo Luminescent Cell Viability Assay (Promega). HEK293 cells plated in 384-well plates were treated with varying concentrations of small molecule and incubated for 48 hours, then treated with CellTiter-Glo reagent and incubated for 10 minutes, at which point the luminescent signal of treated and control wells was measured using a plate reader (Perkin Elmer Wallace).

*E. coli* DNA Gyrase Assays

Supercoiled puc18 plasmid DNA was treated with Topoisomerase I (New England Biolabs) for 30 min at 37° C. to generate relaxed circular puc18 DNA, and then heated to 65° C. to inactivate Topo 1. Relaxed circular puc18 was then treated with *E. coli* DNA gyrase (New England Biolabs) in the presence of water, Cip (100 uM or 500 uM), or BFX (100 uM or 500 uM), incubated at 37° C. for 30 minutes, and then run on a 1% agarose gel without ethidium bromide (EtBr), as EtBr intercalates DNA. After electrophoresis, the gel was stained with EtBr, destained briefly in water, and then imaged with a UV transilluminator.

In Vitro Type VI Secretion Assays

Bt E264 and Bp 1026b strains constitutively expressing VirAG were used for in vitro T6SS-5 secretion experiments. In the case of 5-FC-resistant Bt transposon mutants, complementation with a pBBR plasmid overexpressing VirG was used to induce T6SS-5 expression and secretion in vitro. Overnight bacterial cultures were diluted to an optical density at 600 nm ($OD_{600}$) of 0.05 in LB-NS containing antibiotics when necessary. At an $OD_{600}$ of 0.8-1.2, 0.5 ml aliquots were centrifuged, washed, and resuspended in 200 μL of Laemmli buffer (pellet fractions). The remainder of the culture was centrifuged at 4,750×g for 15 min, and the supernatants were filtered through a 0.2 μM syringe tip filter and precipitated in 10% trichloroacetic acid (TCA) overnight at 4° C. The supernatants were centrifuged at 18,900×g for 15 min at 4° C. and the pellets were washed with 1 ml acetone and resuspended in 200 ul Laemmli buffer (supernatant fractions). Pellet and supernatant samples were normalized according to the $OD_{600}$ of the bacterial culture at the time of harvest. Samples were analyzed by Western Blot as previously described (26).

Microscopy

For actin tail visualization experiments, a 1:1 mixture of HEK293 GFP- and RFP-expressing cells were grown on glass coverslips treated with Matrigel solution, incubated overnight with compound or DMSO, infected with Bt at an MOI of 1, and then washed and fixed 9 hours after infection with 4% paraformaldehyde in PBS containing 3 mM $MgCl_2$ and 10 mM EGTA for 15 min. Cells were permeabilized with 0.2% Triton X-100 in PBS, then incubated with Alexa-Fluor 488-labeled phalloidin, rabbit Bt antiserum, and secondary antibodies in blocking buffer. Permanent mounts of specimens were made with Prolong Gold (Invitrogen), analyzed with a Leica SP5-II AOBS confocal microscope setup, and imaged with a Zeiss Axiovert 40CFL inverted fluorescence microscope fitted with a Canon digital camera. Separate experiments were performed in multiplicate. The proportion of bacteria expressing actin tails was calculated as the number of bacteria associated with an actin tail/total bacteria, per high-powered field.

Library Prep and Whole Genome Sequencing

Libraries were prepared with the Nextera XT kit (Illumina) starting from 1 ng of genomic DNA according to manufacturer's instructions with few modifications. The initial tagmentation step was extended to 8 minutes and the post-PCR purification was performed using a 1:1 ratio of PCR product and AMPure XP beads (Beckman Coulter), Normalized libraries were pooled and sequenced as 100 single-end reads on a HiSeq2500 (Illumina) Rapid Run Mode.

WGS Analysis

Reads for each sample were aligned to the *Burkholderia thailandensis* E264; ATCC 700388 reference genome using BWA-MEM v.0.7.1241039 (Heng Li 2013 arXiv: 1303.3997). An average of 1600 Mb were successfully mapped per sample; minimum was 960 Mb for the wild type sample. Variant discovery was performed with Genome Analysis ToolKit's (GATK) HaplotypeCaller v3.6-0-g8967209 (52). Read alignments for variant regions were inspected for quality assurance using Integrative Genomics Viewer (IGV) (53). The functional impact of variants was predicted using SnpEff 4.2 (54).

In summary, the goal of this study was to identify and characterize small molecule inhibitors of the *Burkholderia* intercellular lifecycle, and to evaluate them as new therapeutic countermeasures. Our cell-based phenotypic screen successfully identified new inhibitors of intercellular spread by Bp and Bm. We identified the mechanism of action for one highly potent molecule, BFX, as inhibition of DNA gyrase, and strongly link the effect of 5-FC, another highly efficacious molecule, to inhibition of T6SS-5 secretion activity. The exceptional in vitro and in vivo efficacy of BFX is intriguing given that fluoroquinolones have not generally been found to be effective for the treatment of melioidosis in animal models or in clinical trials, despite their ability to achieve high intracellular concentrations (43). Our findings suggest that BFX may hold promise as a countermeasure for Bp and Bm, and potentially for other Gram-negative bacteria as well.

Our finding that 5-FC provided a significant survival benefit in a fulminant mouse model, a highly stringent test of efficacy, provides a strong argument for repurposing this FDA-approved antifungal as a new adjunctive therapy for melioidosis. As an FDA-approved drug, 5-FC has a well-established safety and clinical use profile, and is readily accessible in many melioidosis-endemic locale. 5-FC exhibits good bioavailability and ubiquitous distribution in host compartments, including cerebrospinal fluid (37). In addition, 5-FC targets bacterial virulence functions as opposed to growth, and thus may be less prone to resistance selection. Although 5-FC and its derivative F-UR have been found to suppress virulence in another bacterial pathogen, *Pseudomonas aeruginosa*, the underlying mechanism remains unclear (44, 45). For *Burkholderia*, we have shown that 5-FC inhibits the activity of T6SS-5, but not T6SS-5 gene expression. Conversion to 5-FU and then to F-UMP is necessary for selective activity of 5-FC against bacteria, as human cells lack codA and cannot efficiently metabolize 5-FC (37). It is proposed that trace metabolism of 5-FC by the human intestinal microbiota may account for some of the side effects (46).

Since 5-FC has not been used to treat bacterial infections, it remains to be seen whether resistance mechanisms analogous to those in fungi will develop. Fungal resistance to 5-FC is well documented, and precludes the use of 5-FC as a monotherapy. Resistance typically arises from mutations in codB or codA that affect 5-FC uptake and metabolism, or due to increased synthesis of pyrimidines that compete with 5-FC metabolites in the pyrimidine salvage pathway (47, 48). We speculate that similar mechanisms of resistance could arise in bacteria. In addition, our 5-FC resistance screen demonstrated that mutations in tarA can also lead to partial 5-FC resistance, and this is correlated with dysregulation of T6SS-5 activity. Although the assembly of the *Burkholderia* T6SS-5 apparatus occurs in response to activation by VirAG, a two-component sensor-regulator system that senses reduced glutathione in the cytosol (49), the signals that trigger deployment of the contractile T6SS are currently unknown. Our observations suggest that TarAB may be part of a regulatory network that controls such a signal. Interestingly, 5-FC was ineffective against Bm, which lacks TarAB. Unlike Bt and Bp, which inhabit the soil, Bm is mammalian host adapted and has undergone concurrent genome reduction. It is possible that Bm relies on a different strategy for regulation of T6SS-5 that is less reliant on environmental feedback and more suited to its lifestyle as an obligate parasite.

A limitation of our study is that the primary screen was conducted with the BSL-2 surrogate Bt for ease of manipulation. As we later found, the majority of our primary hits in Bt had no effect on Bp or Bm. This was somewhat surprising, as the intercellular lifecycles of Bt, Bp, and Bm are remarkably similar and utilize conserved mechanisms. It is possible that presently unknown differences in the intercellular lifecycles, drug uptake or efflux, or metabolic strategies of these species contributed to this discrepancy. In addition, although our screen was successful in identifying novel therapeutic leads for Bp and/or Bm, a potentially superior but more technically challenging approach would have been to conduct the primary screen in Bp and Bm. Other select-agent drug screening campaigns may benefit from screening with the agent of interest, when feasible, as opposed to surrogate organisms. In addition, although our study examined the efficacy of identified hits in representative Thai and Australian clinical isolates, an extensive strain survey was not conducted. Such a survey might help facilitate translation of these findings to the clinical setting, as Bp is known to be highly genetically variable.

The high-throughput screen described here demonstrates the feasibility of identifying new therapeutic leads for high-consequence select agent bacterial pathogens. This screen may identify additional promising molecules if applied to new compound libraries in the ever-growing chemical space. Cell-based phenotypic screens are a promising approach to drug discovery for intracellular bacterial pathogens, as any compound identified has a priori demonstrated low cytotoxicity, and the ability to traverse the host and bacterial membranes. This is especially advantageous for Gram-negative pathogens, for which the bacterial outer membrane remains a formidable barrier.

Tables

TABLE 1

5-FC and BFX were non-toxic to HEK293 cells at concentrations far exceeding those which effectively inhibit intercellular spread of Bp. Cellular toxicity was assessed using the Celltitre-Glo cell viability assay (see methods).

| Compounds | ED (μM) | TD (μM) |
|---|---|---|
| BFX | 0.1 | >50 |
| 5-FC | 3.1 | >50 |

ED = effective dose (IC100) against Bp, TD = toxic dose (dose at which HEK293 cell growth is significantly affected).

TABLE 2

P. aeruginosa and E. coli are susceptible to BFX. BFX has similar in vitro activity against these organisms as Cip and levofloxacin. BFX was not effective, however, against two different Cip-resistant clinical isolates of P. aeruginosa (P. aeruginosa resistant isolate 1 and 2) and E. coli (E. coli resistant isolate 1 and 2), obtained from the UCLA clinical microbiology laboratory. Shown are minimum inhibitory concentrations, measured by broth microdilution.

|  | Cip MIC (µg/ml) | Levo MIC (µg/ml) | BFX MIC (µg/ml) |
| --- | --- | --- | --- |
| E. coli 25922 | 2 | 4 | 4 |
| E. coli resistant isolate 1 | >7 | >7 | >7 |
| E. coli resistant isolate 2 | >7 | >7 | >7 |
| P. aueruginosa ATCC 27853 | 4 | 5 | 4 |
| P. aeruginosa resistant isolate 1 | >7 | >7 | >7 |
| P. aeruginosa resistant isolate 2 | >7 | >7 | >7 |
| S. aureus ATCC 29213 | >7 | >7 | >7 |
| S. aureus resistant isolate 1 | >7 | >7 | >7 |
| S. aureus resistant isolate 2 | >7 | >7 | >7 |

TABLE 3

Like Cip, BFX is prone to efflux by BpeEF-OprC. BFX shows similar in vitro activity as Cip against Bp82, the attenuated and select agent excluded derivative of commonly used virulent strain 1026b, which expresses only the AmrAB-OprA efflux pump (Podnecky et at. 2017). It is ineffective, however, against three derivatives known to express BpeEF-OprC due to regulatory mutations (Podnecky et al. 2017), Bp82.270 (bpe$T_{S280P}$), Bp82.284 (bpe$S_{P295}$) and Bp82.285 (bpe$S_{K267T}$), similar to Cip. The observed efficacy against AmrAB-OprA expressing Bp82 suggests that BFX is not a substrate for this pump, as has previously been shown for Cip.

| Strain MIC (μg/ml) | Ciprofloxacin | Burkfloxacin |
|---|---|---|
| Bp82 (BpeEF-OprC-) | 1 | 2 |
| Bp82.270 (BpeEF-OprC+) | 16 | 32 |
| Bp82.284 (BpeEF-OprC+) | 16 | 32 |
| Bp82.285 (BpeEF-OprC+) | 16-32 | 32 |

REFERENCES

1. M. Kaestli et al., Out of the ground: aerial and exotic habitats of the melioidosis bacterium *Burkholderia pseudomallei* in grasses in Australia. *Environmental microbiology*, (2011).
2. J. L. Ginther et al., Identification of *Burkholderia pseudomallei* Near-Neighbor Species in the Northern Territory of Australia. *PLoS neglected tropical diseases* 9, e0003892 (2015).
3. W. J. Wiersinga, B. J. Currie, S. J. Peacock, Melioidosis. *The New England journal of medicine* 367, 1035-1044 (2012).
4. B. J. Currie, M. Kaestli, Epidemiology: A global picture of melioidosis. *Nature* 529, 290-291 (2016).
5. L. B. Randall, K. Dobos, K. M. Papp-Wallace, R. A. Bonomo, H. P. Schweizer, Membrane Bound PenA beta-lactamase of *Burkholderia pseudomallei. Antimicrobial agents and chemotherapy*, (2015).
6. N. L. Podnecky, V. Wuthiekanun, S. J. Peacock, H. P. Schweizer, The BpeEF-OprC efflux pump is responsible for widespread trimethoprim resistance in clinical and environmental *Burkholderia pseudomallei* isolates. *Antimicrobial agents and chemotherapy* 57, 4381-4386 (2013).
7. H. P. Schweizer, Mechanisms of antibiotic resistance in *Burkholderia pseudomallei*: implications for treatment of melioidosis. *Future Microbiol* 7, 1389-1399 (2012).
8. C. Chewapreecha et al., Global and regional dissemination and evolution of *Burkholderia pseudomallei. Nat Microbiol* 2, 16263 (2017).
9. K. E. Van Zandt, M. T. Greer, H. C. Gelhaus, Glanders: an overview of infection in humans. *Orphanet journal of rare diseases* 8, 131 (2013).
10. A. Srinivasan et al., Glanders in a military research microbiologist. *The New England journal of medicine* 345, 256-258 (2001).
11. R. Stone, Infectious disease. Racing to defuse a bacterial time bomb. *Science* 317, 1022-1024 (2007).
12. D. A. Dance, in *Bioterrorism and Infectious Agents*. (Springer Science, New York, 2005).
13. L. A. Morici, J. Heang, T. Tate, P. J. Didier, C. J. Roy, Differential susceptibility of inbred mouse strains to *Burkholderia thailandensis* aerosol infection. *Microb Pathog* 48, 9-17 (2010).
14. A. Sawana, M. Adeolu, R. S. Gupta, Molecular signatures and phylogenomic analysis of the genus *Burkholderia*: proposal for division of this genus into the emended genus *Burkholderia* containing pathogenic organisms and a new genus Paraburkholderia gen. nov. harboring environmental species. *Front Genet* 5, 429 (2014).
15. A. Haraga, T. E. West, M. J. Brittnacher, S. J. Skerrett, S. I. Miller, *Burkholderia thailandensis* as a model system for the study of the virulence-associated type III secretion system of *Burkholderia pseudomallei. Infection and immunity* 76, 5402-5411 (2008).
16. D. Limmathurotsakul et al., Predicted global distribution of *Burkholderia pseudomallei* and burden of melioidosis. *Nat Microbiol* 1, (2016).
17. B. J. Currie, L. Ward, A. C. Cheng, The epidemiology and clinical spectrum of melioidosis: 540 cases from the 20 year Darwin prospective study. *PLoS neglected tropical diseases* 4, e900 (2010).
18. B. Maharjan et al., Recurrent melioidosis in patients in northeast Thailand is frequently due to reinfection rather than relapse. *J Clin Microbiol* 43, 6032-6034 (2005).
19. D. Limmathurotsakul et al., Increasing incidence of human melioidosis in Northeast Thailand. *The American journal of tropical medicine and hygiene* 82, 1113-1117 (2010).
20. N. L. Podnecky et al., Mechanisms of Resistance to Folate Pathway Inhibitors in *Burkholderia pseudomallei*: Deviation from the Norm. *MBio* 8, (2017).
21. D. S. Sarovich et al., Raising the Stakes: Loss of Efflux Pump Regulation Decreases Meropenem Susceptibility in *Burkholderia pseudomallei. Clinical infectious diseases: an official publication of the Infectious Diseases Society of America* 67, 243-250 (2018).
22. J. E. Cummings, R. A. Slayden, Transient In Vivo Resistance Mechanisms of *Burkholderia pseudomallei* to Ceftazidime and Molecular Markers for Monitoring Treatment Response. *PLoS neglected tropical diseases* 11, e0005209 (2017).
23. I. J. Toesca, Bulterys P. L., DeShazer D., Miller J. F., French C. T., Intercellular fusion mediated by the T6SS-5 membrane puncturing spike complex is associated with pathogenesis of *Burkholderia pseudomallei. In Preparation*, (2018).
24. C. T. French et al., Dissection of the *Burkholderia* intracellular life cycle using a photothermal nanoblade. *Proceedings of the National Academy of Sciences of the United States of America* 108, 12095-12100 (2011).

25. E. E. Galyov, P. J. Brett, D. DeShazer, Molecular insights into *Burkholderia pseudomallei* and *Burkholderia mallei* pathogenesis. *Annual review of microbiology* 64, 495-517 (2010).
26. I. J. Toesca, C. T. French, J. F. Miller, The Type VI secretion system spike protein VgrG5 mediates membrane fusion during intercellular spread by *pseudomallei* group *Burkholderia* species. *Infection and immunity* 82, 1436-1444 (2014).
27. L. Whiteley et al., Entry, Intracellular Survival, and Multinucleated-Giant-Cell-Forming Activity of *Burkholderia pseudomallei* in Human Primary Phagocytic and Nonphagocytic Cells. *Infection and immunity* 85, (2017).
28. S. Schwarz et al., VgrG-5 is a *Burkholderia* type VI secretion system-exported protein required for multinucleated giant cell formation and virulence. *Infection and immunity* 82, 1445-1452 (2014).
29. I. J. Toesca, Miller J. F., French C. T., Intercellular Fusion Mediated by the T6SS-5 membrane puncturing spike complex is Crucial for Virulence by *Pseudomallei*-group *Burkholderia*. *In Preparation*, (2016).
30. W. J. Wiersinga, T. van der Poll, N. J. White, N. P. Day, S. J. Peacock, Melioidosis: insights into the pathogenicity of *Burkholderia pseudomallei*. *Nat Rev Microbiol* 4, 272-282 (2006).
31. D. J. Payne, M. N. Gwynn, D. J. Holmes, D. L. Pompliano, Drugs for bad bugs: confronting the challenges of antibacterial discovery. *Nat Rev Drug Discov* 6, 29-40 (2007).
32. K. Lewis, Platforms for antibiotic discovery. *Nat Rev Drug Discov* 12, 371-387 (2013).
33. B. Spellberg, D. N. Gilbert, The future of antibiotics and resistance: a tribute to a career of leadership by John Bartlett. *Clin Infect Dis* 59 Suppl 2, S71-75 (2014).
34. D. M. Estes, S. W. Dow, H. P. Schweizer, A. G. Tones, Present and future therapeutic strategies for melioidosis and glanders. *Expert Rev Anti Infect Ther* 8, 325-338 (2010).
35. S. Bazile, N. Moreau, D. Bouzard, M. Essiz, Relationships among antibacterial activity, inhibition of DNA gyrase, and intracellular accumulation of 11 fluoroquinolones. *Antimicrobial agents and chemotherapy* 36, 2622-2627 (1992).
36. L. B. Randall, E. Georgi, G. H. Genzel, H. P. Schweizer, Finafloxacin overcomes *Burkholderia pseudomallei* efflux-mediated fluoroquinolone resistance. *J Antimicrob Chemother* 72, 1258-1260 (2017).
37. J. E. Nett, D. R. Andes, Antifungal Agents: Spectrum of Activity, Pharmacology, and Clinical Indications. *Infect Dis Clin North Am* 30, 51-83 (2016).
38. WHO. (2017), vol. 2018.
39. Y. Chen et al., Characterization and analysis of the *Burkholderia pseudomallei BsaN virulence regulon*. *BMC microbiology* 14, 206 (2014).
40. A. Vermes, H. J. Guchelaar, J. Dankert, Flucytosine: a review of its pharmacology, clinical indications, pharmacokinetics, toxicity and drug interactions. *J Antimicrob Chemother* 46, 171-179 (2000).
41. L. A. Gallagher et al., Sequence-defined transposon mutant library of *Burkholderia thailandensis*. *MBio* 4, e00604-00613 (2013).
42. K. Ishida, T. Lincke, S. Behnken, C. Hertweck, Induced biosynthesis of cryptic polyketide metabolites in a *Burkholderia thailandensis* quorum sensing mutant. *J Am Chem Soc* 132, 13966-13968 (2010).
43. D. Dance, Treatment and prophylaxis of melioidosis. *Int J Antimicrob Agents* 43, 310-318 (2014).
44. F. Imperi et al., Repurposing the antimycotic drug flucytosine for suppression of *Pseudomonas aeruginosa* pathogenicity. *Proceedings of the National Academy of Sciences of the United States of America* 110, 7458-7463 (2013).
45. D. R. Kirienko, A. V. Revtovich, N. V. Kirienko, A High-Content, Phenotypic Screen Identifies Fluorouridine as an Inhibitor of Pyoverdine Biosynthesis and *Pseudomonas aeruginosa* Virulence. *mSphere* 1, (2016).
46. B. E. Harris, B. W. Manning, T. W. Federle, R. B. Diasio, Conversion of 5-fluorocytosine to 5-fluorouracil by human intestinal microflora. *Antimicrobial agents and chemotherapy* 29, 44-48 (1986).
47. W. W. Hope, L. Tabernero, D. W. Denning, M. J. Anderson, Molecular mechanisms of primary resistance to flucytosine in *Candida albicans*. *Antimicrobial agents and chemotherapy* 48, 4377-4386 (2004).
48. M. S. Chandra J, Ghannoum M A, in *Antimicrobial Drug Resistance*. (Humana Press, 2009), pp. 313-326.
49. J. Wong, Y. Chen, Y. H. Gan, Host Cytosolic Glutathione Sensing by a Membrane Histidine Kinase Activates the Type VI Secretion System in an Intracellular Bacterium. *Cell host & microbe* 18, 38-48 (2015).
50. N. Anuntagool et al., Monoclonal antibody-based rapid identification of *Burkholderia pseudomallei* in blood culture fluid from patients with community-acquired septicaemia. *Journal of medical microbiology* 49, 1075-1078 (2000).
51. N. Samosornsuk et al., Short report: evaluation of a monoclonal antibody-based latex agglutination test for rapid diagnosis of septicemic melioidosis. *The American journal of tropical medicine and hygiene* 61, 735-737 (1999).
52. A. McKenna et al., The Genome Analysis Toolkit: a MapReduce framework for analyzing next-generation DNA sequencing data. *Genome Res* 20, 1297-1303 (2010).
53. J. T. Robinson et al., Integrative genomics viewer. *Nat Biotechnol* 29, 24-26 (2011).
54. P. Cingolani et al., A program for annotating and predicting the effects of single nucleotide polymorphisms, SnpEff: SNPs in the genome of *Drosophila melanogaster* strain w1118; iso-2; iso-3. *Fly (Austin)* 6, 80-92 (2012).

PUBLICATIONS

All publications mentioned herein (e.g. those listed above and Bulterys et al., Proc Natl Acad Sci USA. 2019 Sep. 10; 116(37):18597-18606. doi: 10.1073/pnas.1906388116000) are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification. The following references include descriptions of methods and materials in this field of technology.

CONCLUSION

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A method of inhibiting intercellular spreading of *Burkholderia pseudomallei* or *Burkholderia mallei* bacteria, the method comprising contacting the *Burkholderia pseudomallei* or *Burkholderia mallei* bacteria with Burkfloxacin;

wherein the *Burkholderia pseudomallei* or *Burkholderia mallei* bacteria are contacted with amounts of Burkfloxacin sufficient to inhibit intercellular spreading of the *Burkholderia pseudomallei* or *Burkholderia mallei* bacteria; and Burkfloxacin is administered to a patient diagnosed with melioidosis or glanders disease.

2. The method of claim 1, wherein the agent is disposed within a composition further comprising a pharmaceutically acceptable carrier selected from at least one of: a pH adjusting agent, a buffering agent, a tonicity adjusting agent, a wetting agent, an antioxidant, a viscosity-increasing agent or a preservative.

3. The method of claim 2, wherein the agent is contacted with the *Burkholderia pseudomallei* or *Burkholderia mallei* bacteria growing in vivo.

4. The method of claim 1, wherein:

the patient is administered the agent at doses between 1 mg/kg/day and 250 mg/kg/day; and/or agent is administered to the patient at least 1, 2 or 3 times/day for at least 4, 5, 6, or 7 days.

5. The method of claim 1, wherein concentrations of at least 1 µM or 5 µM or 10 µM of the agent comprises amounts of agent(s) sufficient to inhibit intercellular spreading of the *Burkholderia pseudomallei* or *Burkholderia mallei* bacteria.

6. The method of claim 1, wherein the agent inhibits intercellular spreading of *Burkholderia pseudomallei* or *Burkholderia mallei* bacteria to an extent greater than that observed with ceftazidime at concentrations of 0.125 µM to 8 µM.

* * * * *